(12) United States Patent
Amin

(10) Patent No.: US 12,285,181 B2
(45) Date of Patent: *Apr. 29, 2025

(54) METHODS FOR FORMING A TUNNEL IN BONE

(71) Applicant: Integrity Medical Services Inc., Yorba Linda, CA (US)

(72) Inventor: Nirav H. Amin, Yorba Linda, CA (US)

(73) Assignee: Integrity Medical Services Inc., Yorba Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/770,306

(22) Filed: Jul. 11, 2024

(65) Prior Publication Data

US 2025/0017605 A1 Jan. 16, 2025

Related U.S. Application Data

(60) Provisional application No. 63/513,295, filed on Jul. 12, 2023.

(51) Int. Cl.
*A61B 17/17* (2006.01)
*A61B 17/04* (2006.01)
*A61F 2/08* (2006.01)

(52) U.S. Cl.
CPC ...... *A61B 17/1796* (2013.01); *A61B 17/0482* (2013.01); *A61B 17/171* (2013.01); *A61B 17/1714* (2013.01); *A61B 17/1717* (2013.01); *A61F 2/0805* (2013.01); *A61F 2002/0852* (2013.01)

(58) Field of Classification Search
CPC . A61B 17/17; A61B 17/1714; A61B 17/1717; A61B 17/1725; A61B 17/1675
See application file for complete search history.

(56) References Cited

U.S. PATENT DOCUMENTS

| | | | |
|---|---|---|---|
| 4,922,897 A | 5/1990 | Sapega et al. | |
| 5,112,337 A | 5/1992 | Paulos et al. | |
| 5,154,720 A | 10/1992 | Trott et al. | |
| 5,163,940 A | 11/1992 | Bourque | |
| 5,201,741 A | 4/1993 | Dulebohn | |
| 5,330,468 A * | 7/1994 | Burkhart | A61B 17/1778 606/96 |
| 5,374,269 A | 12/1994 | Rosenberg | |
| 5,417,684 A | 5/1995 | Jackson et al. | |

(Continued)

FOREIGN PATENT DOCUMENTS

| | | |
|---|---|---|
| CN | 104083204 | 6/2016 |
| CN | 208081271 | 11/2018 |

(Continued)

OTHER PUBLICATIONS

Arthrex, FiberSnare® Suture. Undated; downloaded Jul. 17, 2024 from https://www.arthrex.com/knee/fibersnare; 4 pages.

(Continued)

*Primary Examiner* — Anu Ramana
(74) *Attorney, Agent, or Firm* — Knobbe Martens Olson & Bear, LLP

(57) ABSTRACT

An orthopedic tool includes a main body and a reference member. The reference member may be configured to engage an anatomical feature of a patient, such as the patient's bone. The angle of the reference member may be adjusted using a knob.

24 Claims, 26 Drawing Sheets

(56) References Cited

U.S. PATENT DOCUMENTS

| | | | |
|---|---|---|---|
| 5,501,692 A | 3/1996 | Riza | |
| 5,709,697 A | 1/1998 | Ratcliff et al. | |
| 5,817,111 A | 10/1998 | Riza | |
| 5,865,834 A | 2/1999 | McGuire | |
| 5,895,389 A | 4/1999 | Schenk | |
| 5,993,451 A | 11/1999 | Burkhart | |
| 6,022,360 A | 2/2000 | Reimels et al. | |
| 6,063,088 A * | 5/2000 | Winslow | A61F 2/4611 606/279 |
| 6,120,511 A | 9/2000 | Chan | |
| 6,254,605 B1 | 7/2001 | Howell | |
| 6,676,668 B2 | 1/2004 | Mercereau et al. | |
| 7,192,431 B2 | 3/2007 | Hangody et al. | |
| 7,210,881 B2 | 5/2007 | Greenberg | |
| 7,270,663 B2 | 9/2007 | Nakao | |
| 7,575,578 B2 | 8/2009 | Wetzler et al. | |
| 7,578,824 B2 | 8/2009 | Justin et al. | |
| 7,771,483 B2 | 8/2010 | Justin et al. | |
| 8,523,872 B2 | 9/2013 | Ek | |
| 8,690,885 B2 * | 4/2014 | Smith | A61B 17/1714 606/96 |
| 8,740,913 B2 | 6/2014 | Schneider | |
| 8,888,795 B2 | 11/2014 | Chu | |
| 9,023,056 B2 | 5/2015 | Berberich | |
| 9,161,764 B2 | 10/2015 | Smith | |
| 9,232,954 B2 * | 1/2016 | Steiner | A61B 17/1675 |
| 9,451,951 B2 | 9/2016 | Sullivan et al. | |
| 10,098,646 B2 * | 10/2018 | Ardito | A61B 17/1675 |
| 10,492,804 B2 | 12/2019 | Amis et al. | |
| 10,758,251 B2 | 9/2020 | Miller | |
| 10,799,334 B2 | 10/2020 | Smigielski et al. | |
| 10,888,349 B2 | 1/2021 | Pereira et al. | |
| 11,033,283 B2 | 6/2021 | Mirochinik et al. | |
| 11,166,732 B2 | 11/2021 | Maxon et al. | |
| 11,202,641 B2 | 12/2021 | Biton et al. | |
| 11,357,517 B1 | 6/2022 | Amin | |
| 11,471,150 B2 | 10/2022 | Smith et al. | |
| 11,504,140 B2 | 11/2022 | Fallin et al. | |
| 11,903,602 B2 | 2/2024 | Sullivan et al. | |
| 11,986,193 B2 | 5/2024 | Amin | |
| 12,023,049 B2 | 7/2024 | Amin | |
| 12,102,338 B2 | 10/2024 | Amin | |
| 2002/0133165 A1 | 9/2002 | Whittaker et al. | |
| 2004/0176771 A1 | 9/2004 | Schmieding | |
| 2006/0173468 A1 | 8/2006 | Simmon et al. | |
| 2006/0293689 A1 | 12/2006 | Miller et al. | |
| 2007/0233128 A1 | 10/2007 | Schmieding | |
| 2008/0154271 A1 | 6/2008 | Berberich et al. | |
| 2008/0183174 A1 | 7/2008 | Sikora et al. | |
| 2009/0171359 A1 | 7/2009 | Sterrett | |
| 2011/0125156 A1 | 5/2011 | Sharkey | |
| 2011/0166581 A1 | 7/2011 | Van Der Merwe et al. | |
| 2012/0109136 A1 | 5/2012 | Bourque et al. | |
| 2014/0155899 A1 | 6/2014 | Bowman et al. | |
| 2014/0276844 A1 | 9/2014 | Bourque et al. | |
| 2014/0276884 A1 | 9/2014 | Lizardi et al. | |
| 2015/0133941 A1 | 5/2015 | Saylor et al. | |
| 2015/0190147 A1 | 7/2015 | Ferragamo et al. | |
| 2015/0345927 A1 | 12/2015 | Bourque et al. | |
| 2015/0351777 A1 | 12/2015 | Lizardi et al. | |
| 2016/0089161 A1 | 3/2016 | Ardito et al. | |
| 2017/0007279 A1 | 1/2017 | Sharma | |
| 2017/0042556 A1 | 2/2017 | LaPrade et al. | |
| 2017/0189036 A1 | 7/2017 | Rajeev | |
| 2017/0245869 A1 | 8/2017 | Mirochinik | |
| 2018/0153572 A1 | 6/2018 | Fojtik et al. | |
| 2020/0375615 A1 | 12/2020 | Walker | |
| 2022/0110640 A1 | 4/2022 | Kam et al. | |
| 2022/0117720 A1 | 4/2022 | Ng et al. | |
| 2023/0157808 A1 | 5/2023 | Cole et al. | |
| 2025/0009365 A1 | 1/2025 | Amin | |
| 2025/0017719 A1 | 1/2025 | Amin | |

FOREIGN PATENT DOCUMENTS

| | | |
|---|---|---|
| CN | 217853139 U | 11/2022 |
| EP | 2419035 | 7/2017 |
| WO | WO 2018/075615 | 4/2018 |

OTHER PUBLICATIONS

DAIC—Diagnostic and Interventional Cardiology, SentreHeart Receives CE Mark for Lariat Suture Delivery Device. News Article; Oct. 28, 2015; downloaded from https://www.dicardiology.com/content/sentreheart-receives-ce-mark-lariat-suture-delivery-device; 5 pages.

Espejo-Baena et al., Posterior Cruciate Ligament Reconstruction With Hamstring Tendons Using a Suspensory Device for Tibial Fixation and Interference Screw for Femoral Fixation. Arthroscopy Techniques. Feb. 1, 2017;6(1): e213-e218.

Petry A., SutureSnare™ Suture Passer—Product Demonstration; Anthrex Apr. 25, 2016, downloaded from https://www.arthrex.com/resources/VID1-00773-EN/suturesnare-suture-passer on Jul. 17, 2024; 4 pages.

STERIS Healthcare, Lariat® Snare. Product Details, undated, downloaded from https://www.steris.com/healthcare/products/endoscopy-devices/polypectomy-and-tissue-acquisition-devices/lariat-snare; 4 pages.

Yin et al., Transtibial Pull-Out Repair of Converted Radial Tear Adjacent to Medial Meniscus Root. Arthroscopy Techniques.Jan. 1, 2020;9(1): e171-e176.

Zimmer Biomet, SpeedSnare™ Surgical Suture Passer. Website for Healthcare Professionals;undated downloaded on Jul. 17, 2024 from https://www.zimmerbiomet.com/en/products-and-solutions/specialties/sports-medicine/speedsnare-surgical-suture-passer.html, 8 pages.

\* cited by examiner

METHODS FOR FORMING A TUNNEL IN BONE

INCORPORATION BY REFERENCE TO ANY PRIORITY APPLICATIONS

Any and all applications for which a foreign or domestic priority claim is identified in the Application Data Sheet as filed with the present application are hereby incorporated in their entireties by reference under 37 CFR 1.57. In particular, this application claims priority to the U.S. Provisional Application 63/513,295, filed Jul. 12, 2023, which is incorporated by reference herein in its entirety.

TECHNICAL FIELD

The present disclosure relates to the field of surgical methods and devices, and more particularly to arthroscopic ligament repair and/or reconstruction surgery.

BACKGROUND

Desired outcomes for arthroscopic ligament reconstruction or repair surgery are generally achieved by establishing the proper shape and placement of torn tissue. While performing such surgery, a surgeon typically makes a small incision in a patient's skin near the surgical site (e.g., a bone joint) to allow a drill assembly to be placed in the bone joint to create tunnels through the patient's bone, through which the surgeon can reconstruct or repair the torn tissue.

For a meniscal root repair, for example, one approach is to create a tunnel through the patient's tibia for the passing of a suture or wire. The suture is passed to the location of repair, and the meniscus is repaired with a button, anchor, or other suitable method of fixation. In some instances, the root repair may involve isolating the root and repositioning the root into a more suitable anatomical position. The current system of meniscus root guide requires pre-operative equipment to be sterilized and processed for the surgical procedure. Often, the MRI is unable to detect the meniscus root tear, leading to challenges with the meniscus root repair.

Accordingly, there is a need for devices and methods to help guide and properly align meniscal root repair procedures. There is a need for disposal guide to allow the meniscus root repair procedure to be perform during any surgical case without prior planning due to the nature of the tears and location of the tears.

SUMMARY

In some examples, a method of forming a tunnel in bone can include: providing an orthopedic tool, wherein the orthopedic tool includes: a main body; a drill guide having a proximal end, a distal end, and a lumen extending from the proximal end to the distal end, the drill guide configured to engage the main body; a reference member having a distal end, the reference member configured to engage the main body, and the reference member including an engagement component on the distal end, the engagement component configured to engage a patient's bone; and a reference member knob configured to engage the main body and the reference member; adjusting, with the reference member knob, an angle of the reference member relative to the drill guide; introducing the reference member to a surgical site such that the reference member engages the patient's bone; introducing the drill guide to a surgical site such that the drill guide engages the patient's bone; and advancing a drill pin through the lumen of the drill guide such that a tunnel is formed in the patient's bone. In some examples, the reference member is moveable with respect to the main body.

In some examples, the method can include positioning a plurality of locking components to engage the drill guide such that the drill guide is locked in place with respect to the main body. In some examples, the method can include advancing a suture through the drill guide and the tunnel. In some examples, the method can include advancing the suture through the engagement component, wherein the engagement component is elliptical. In some examples, the method can include forcing an elliptical drill bit on the distal end of the drill guide into the patient's bone. In some examples, positioning the plurality of locking components such that the drill guide is locked in place with respect to the main body includes rotating the drill guide such that a plurality of grooves of the drill guide engages at least one locking component of the plurality of locking components.

In some examples, an orthopedic tool can include: a main body; a drill guide having a proximal end, a distal end, and a lumen extending from the proximal end to the distal end, the drill guide configured to engage the main body; a reference member having a distal end, the reference member configured to engage the main body, and the reference member including an engagement component on the distal end, the engagement component configured to engage a patient's bone; and a reference member knob configured to engage the main body and the reference member, the reference member knob configured to adjust a position of the reference member relative to the main body.

In some examples, the orthopedic tool can include a plurality of locking components configured to selectively lock the drill guide in place with respect to the main body. In some examples, the plurality of locking components include a plurality of spring-loaded caps configured to engage a threaded portion of the drill guide. In some examples, the plurality of locking components include a ball plunger configured to engage the drill guide. In some examples, the engagement component includes curved components extending laterally from the distal end of the reference member. In some examples, the engagement component includes an elliptical component on the distal end of the reference member. In some examples, the orthopedic tool can include an elliptical drill bit on a distal end of the drill guide. In some examples, the reference member knob is configured to adjust an angle of the reference member relative to the drill guide. In some examples, the reference member includes a first arm configured to engage the main body, a second arm configured to engage the patient's bone, and an angle between the first arm and the second arm. In some examples, the engagement component includes a fork component.

In some examples, disclosed herein is a meniscal root repair guide, comprising one or more of: a drill guide having a proximal end, a distal end, and a channel extending from the proximal end to the distal end; a handle configured to engage the drill guide; a first securement component configured to engage the drill guide and the handle; a reference member configured to engage the handle and a patient's tibia; and a second securement component configured to engage the reference member and the handle.

In examples, the reference member comprises a first arm configured to engage the handle, a second arm configured to engage the patient's tibia, and an angle between the first arm and the second arm.

In examples, the reference member comprises a guide assistance feature at a distal end of the second arm.

In examples, the guide assistance feature comprises a fork feature.

In examples, the drill guide comprises a screw.

In some examples, the drill guide channel is configured to allow passage of a portion of a drill pin from the drill guide proximal end to the drill guide distal end.

In certain examples, the drill guide channel is configured to allow passage of a portion of a drill pin having an outer diameter of about 2.4 mm.

In some examples, an inner diameter of the drill guide channel is larger than 2.4 mm.

In particular examples, the first securement component comprises a screw.

In some examples, the first securement component comprises a knurled thumbscrew.

In some examples, the first securement component comprises a sliding securement component.

In some examples, the drill guide comprises an engagement feature configured to engage the sliding securement component.

In some examples, the drill guide comprises a plurality of engagement features configured to engage the sliding securement component.

In examples, the second securement component comprises a screw.

In examples, the second securement component comprises a knurled thumbscrew.

In examples, disclosed herein is a meniscal root repair kit, comprising one or more of: a meniscal root repair guide, wherein the meniscal root repair guide comprises: a drill guide having a proximal end, a distal end, and a channel extending from the proximal end to the distal end; a handle configured to engage the drill guide; a first securement component configured to engage the drill guide and the handle; a reference member configured to engage the handle and a patient's tibia; and a second securement component configured to engage the reference member and the handle; a curette configured to remove tissue from a surgical site; a drill pin; a cannulated drill bit; and a delivery device configured to deliver a fixation component to the surgical site.

In some examples, the curette is configured to remove cartilage from the surgical site.

In examples, the drill pin comprises an outer diameter of about 2.4 mm.

In some examples, the drill pin comprises an axial length of about 100-180 mm.

In certain examples, the cannulated drill bit comprises a proximal end, a distal end, and a channel extending from the drill bit proximal end to the drill bit distal end.

In some examples, the channel of the cannulated drill bit is configured to allow passage of a portion of the delivery device through the channel of the cannulated drill bit.

In some examples, the delivery device comprises a suture passer.

In some examples, the delivery device is configured to deliver a suture to the surgical site.

In some examples, the delivery device is configured to deliver a wire to the surgical site.

In some examples, disclosed herein is a method of repairing a meniscal root, comprising one or more of: providing a meniscal root repair guide, wherein the meniscal root repair guide comprises: a drill guide having a proximal end, a distal end, and a channel extending from the proximal end to the distal end; a handle configured to engage the drill guide; a first securement component configured to engage the drill guide and the handle; a reference member configured to engage the handle and a patient's tibia; and a second securement component configured to engage the reference member and the handle; introducing the reference member to a surgical site such that the reference member engages a tibial feature; advancing the drill guide to an extended state, wherein, in the extended state, the drill guide is directed substantially towards the surgical site; positioning the first securement component such that the drill guide and the handle are securely engaged; and advancing a drill pin through the channel of the drill guide such that a tunnel is formed in a tibia.

In some examples, advancing the drill pin through the channel of the drill guide comprises advancing a drill pin having an outer diameter of about 2.4 mm through the channel of the drill guide.

In some examples, the method of repairing a meniscal root comprises advancing a cannulated drill bit over the drill pin, wherein the cannulated drill bit comprises a proximal end, a distal end, and a channel extending therebetween.

In some examples, the method of repairing a meniscal root comprises passing a suture through the channel of the cannulated drill bit.

In some examples, the method of repairing a meniscal root comprises passing a wire through the channel of the cannulated drill bit.

DETAILED DESCRIPTION

Examples disclosed herein relate to devices, systems, and methods of meniscal root repair. Some examples of devices disclosed herein relate to a meniscal root repair guide configured to help align meniscal root repair procedures. Some examples disclosed herein relate to kits for use in meniscal root repair. Some examples disclosed herein relate to methods of guided meniscal root repair.

Meniscal Root Repair Guide

Figure 1:
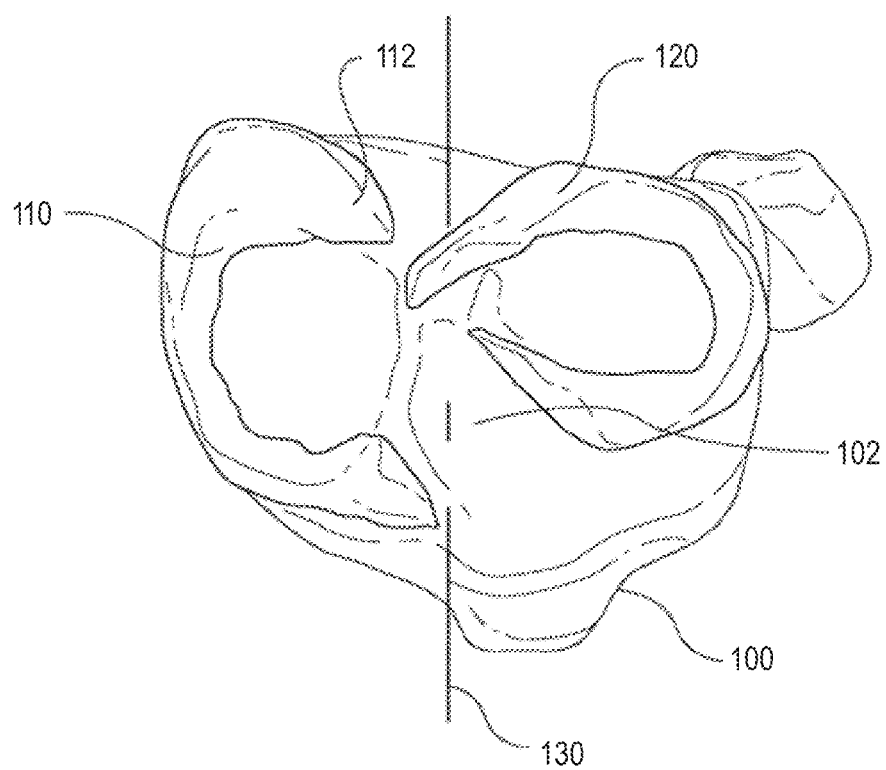
FIG. 1 illustrates a top plan view of a tibia that shows meniscal tissue, including damaged medial and or lateral meniscal tissue, whether anterior or posterior, which can be used for radial tear of the midbody of the lateral meniscus.
Figure 2:
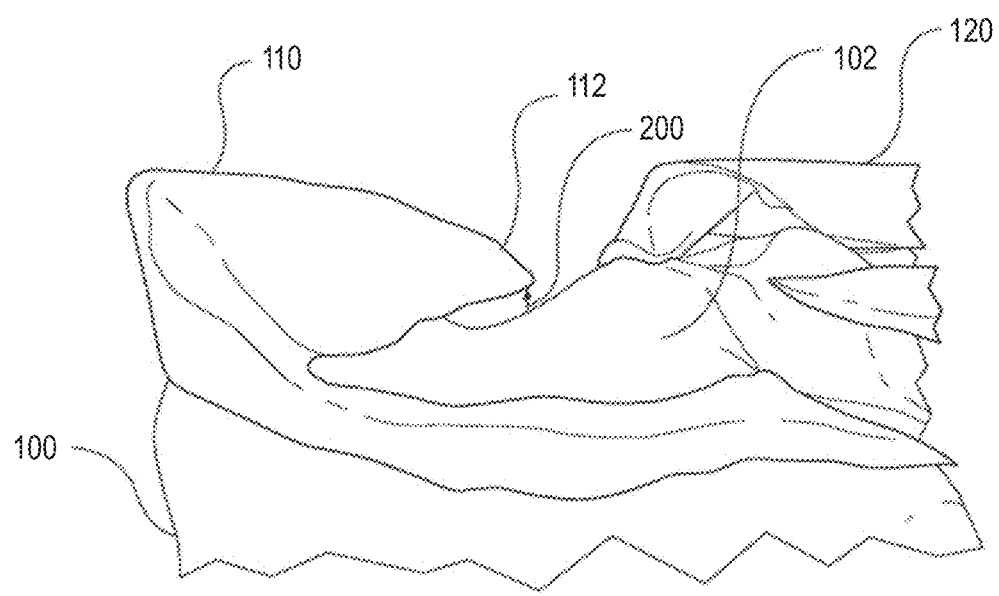
FIG. 2 illustrates a side perspective view of the tibia and medial meniscus shown in FIG. 1.

FIG. 1 illustrates a tibia 100, a tibial plateau 102, a medial meniscus 110, and a lateral meniscus 120. FIG. 2 illustrates a posterior root 112 of the medial meniscus 110 separated from the tibial plateau 102 by a distance illustrated in FIG. 2 by arrow 200, and consequently in need of repair. A plateau line 130 along an average plane of the tibial plateau 102 is shown in FIG. 1. The plateau line 130 and the tibial plateau 102 as used herein will refer to a substantial average plane, or predominant plane, of the superior portion of the tibia 100 boney surfaces of the tibial plateau 102. Because the superior portion of the tibia 100 boney surfaces are irregular, such a substantial average plane, or predominant plane, is understood by those skilled in the art to serve as an angular reference for a tibia. The illustrated plateau line 130 is drawn along the tibial plateau 102 in a substantially anterior-posterior direction at an approximate medial-lateral midline of the tibia 100. The devices, systems, and methods herein can be used to drill to the medial meniscus root or the lateral meniscus root. The devices, systems, and methods herein can be used to drill to the anterior and/or posterior root.

Methods and devices described herein are illustrated in association with meniscal root repair; however, the methods and devices described herein may be equally applicable to other repairs. Reattachment or repair may be accomplished, for example and without limitation, on various parts of the medial meniscus 110, on various parts of the lateral meniscus 120, or any various other soft tissue structures. The soft tissue repaired or reattached may be, for example and without limitation, cartilage, ligaments, tendons, or any combination or part of these soft tissues or others. Bones to which soft tissue may be reattached include, for example and without limitation, a tibia, femur, patella, humerus, radius, or any combination or part of these bones or others. Soft tissue coupled, attached, reattached, repaired, or brought into contact with bone in various examples may consequently be given the opportunity to heal.

FIGS. 3A-3D illustrate various views of an embodiment of a meniscal root repair guide 300, also referred to herein as a repair guide 300. The repair guide 300 may include a guide handle 310, a drill guide 320, and a meniscal guide member 330. The meniscal guide member 330 may also be referred to as a reference member 330. The repair guide 300 may also include securement features 340 and 342, which may also be referred to as a drill guide securement feature 340 and a reference member securement feature 342.

The guide handle 310 may engage the drill guide 320. For example, a through hole in the guide handle 310 may allow engagement of the guide handle 310 and the drill guide 320. Securement feature 340 may be used to secure, connect, fasten, or otherwise couple the guide handle 310 and the drill guide 320.

The guide handle 310 may also engage the reference member 330. Securement feature 342 may be used to secure, connect, fasten, or otherwise couple the guide handle 310 and the reference member 330. In some examples, securement features 340 and 342 may be screws. For example, in some examples, securement features 340 and 342 may be knurled thumbscrews.

A repair guide 300 configured of individual, or modular, components may advantageously promote interchangeability, replaceability, and disposability of the components of the repair guide 300.

Figure 3A:
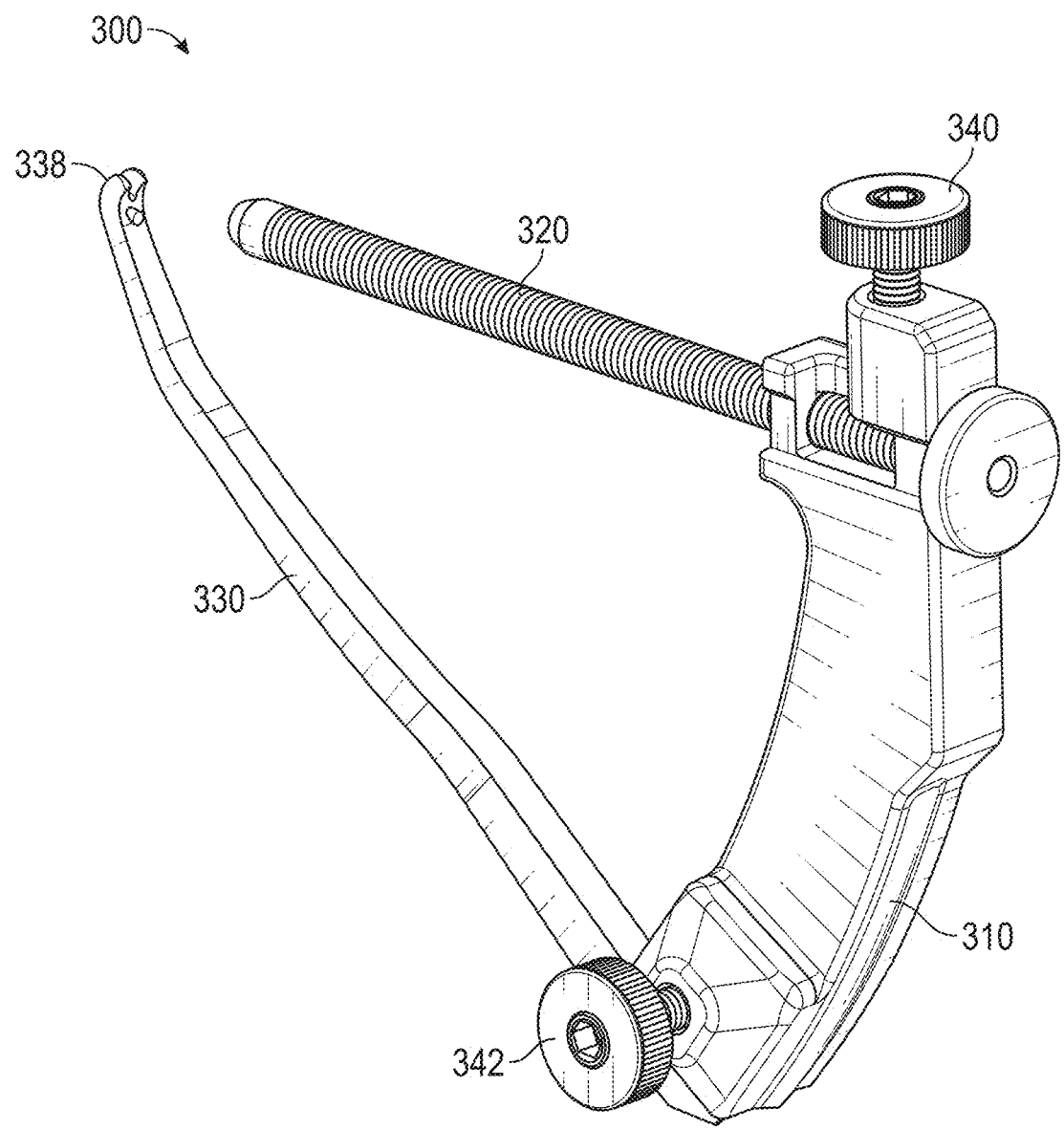
FIG. 3A illustrates a perspective view of an embodiment of a meniscal root repair guide.
Figure 3B:
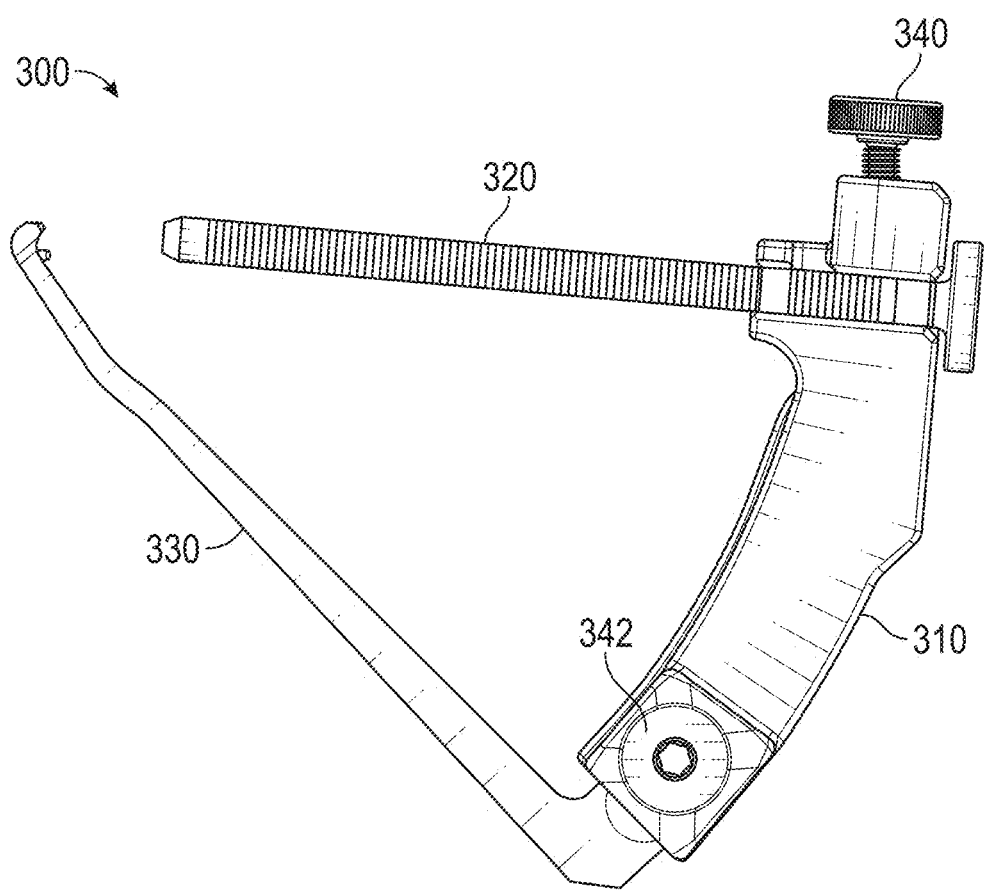
FIG. 3B illustrates a side view of the embodiment of a meniscal root repair guide shown in FIG. 3A.
Figure 3C:
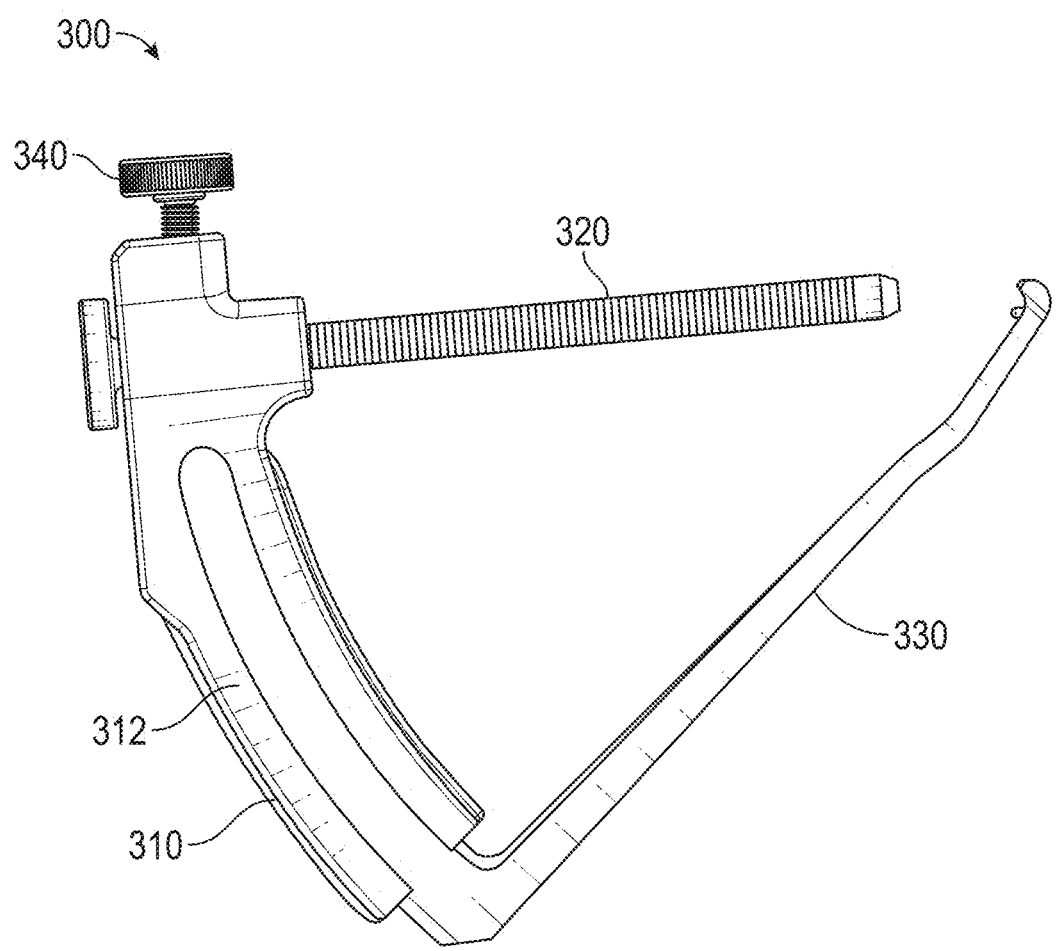
FIG. 3C illustrates a side view of the embodiment of a meniscal root repair guide shown in FIG. 3A.
Figure 3D:
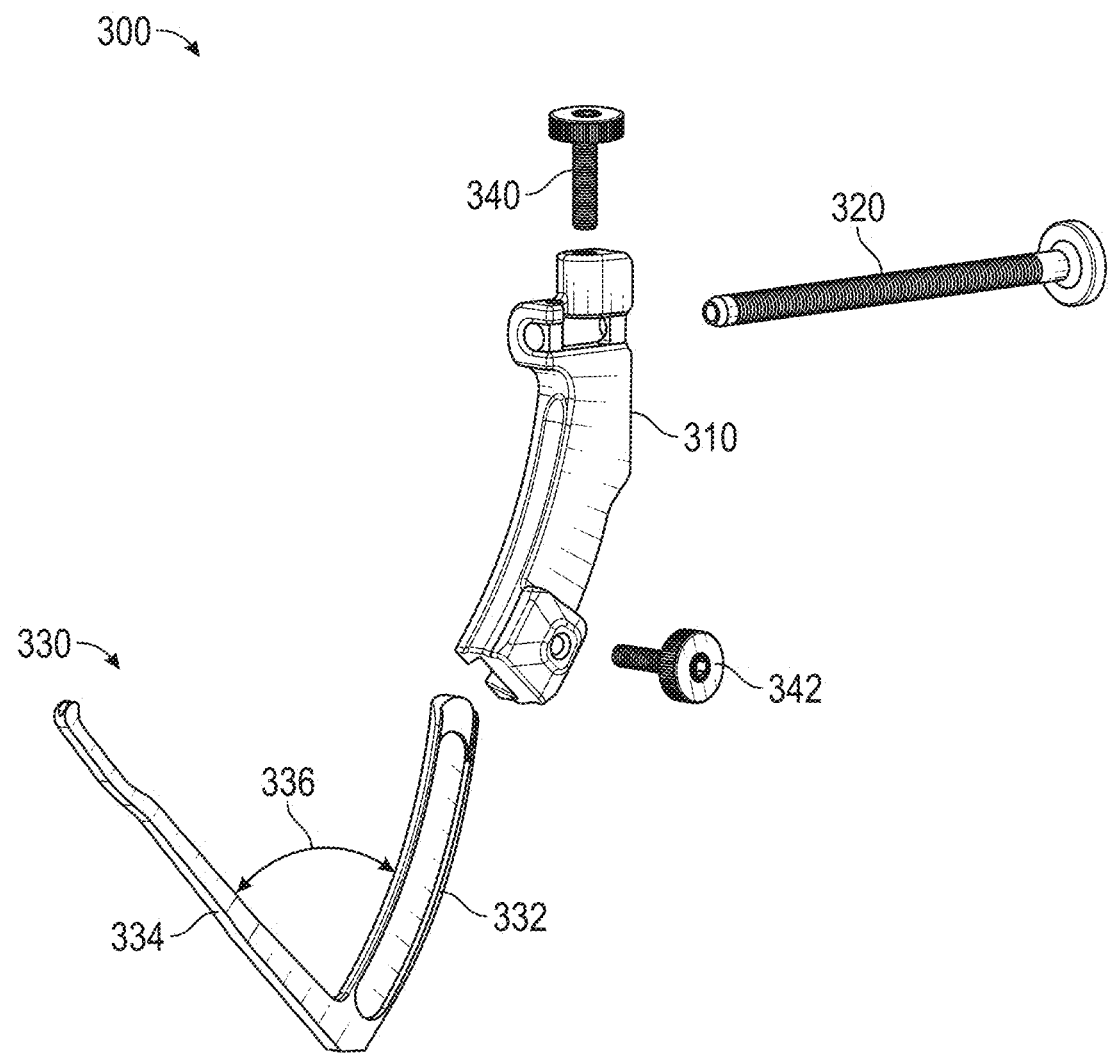
FIG. 3D illustrates an exploded view of the embodiment of the meniscal root repair guide shown in FIG. 3A.

As depicted in FIG. 3D, the reference member 330 may include a first arm 332 and a second arm 334. The first arm 332 and the second arm 334 may define an angle 336. The angle 336 can be any desired angle to provide optimal anatomic fixation of the meniscus root.

The first arm 332 of the reference member 330 may be configured to engage the handle 310. In some examples, as depicted in FIG. 3C, the first arm 332 of the reference member 330 may engage a slot 312 of the handle 310. A securement feature 342 may be used to secure, connect, fasten, or otherwise couple the first arm 332 of the reference member 330 to the handle 310.

The second arm 334 of the reference member 330 may be configured to engage a patient's anatomical features. For example, the second arm 334 may be configured to engage the patient's tibia 100. The second arm 334 may be configured to engage the tibial plateau 102 of the patient's tibia 100. Engagement between the second arm 334 and the patient's tibia 100 may advantageously help to align subsequent meniscal root repair procedures, as more fully described below.

In some examples, the second arm 334 may include a guide assistance feature 338 at the tip of the second arm 334, as depicted in FIG. 3A. For example, the guide assistance feature 338 may include a fork feature, such as a forked tip at the tip of the second arm 334. The guide assistance feature 338 may be configured to engage an anatomical feature of the patient. For example, the guide assistance feature 338 may be sized and shaped such that it engages a portion of the patient's tibia 100. The guide assistance feature 338 having a forked feature may advantageously give the surgeon improved visual access while placing the meniscal root guide 300 and performing meniscal root repair procedures.

For example, a forked feature at the tip of the second arm 334 may give the surgeon visual access from an intra articular camera view.

The reference member 330 may comprise a rigid material. The reference member 330 may be substantially flat, or thin, which may advantageously reduce the risk of injury or damage to a patient when the reference member 330 is inserted into the patient.

Figure 4C:
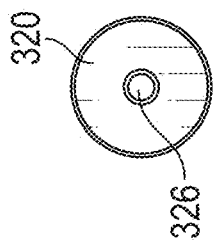
FIG. 4C illustrates a front view of the embodiment of the drill guide shown in FIG. 4A.
Figure 4A:
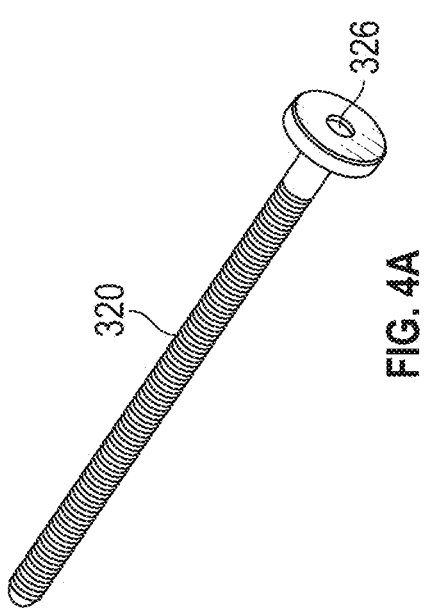
FIG. 4A illustrates a perspective view of an embodiment of a drill guide.
Figure 4B:
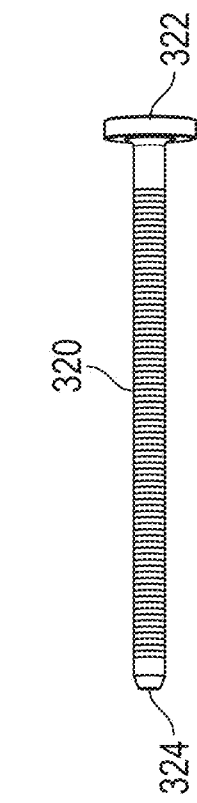
FIG. 4B illustrates a side view of the embodiment of the drill guide shown in FIG. 4A.

FIGS. 4A-4C illustrate an embodiment of a drill guide 320. In some examples, the drill guide 320 may comprise a screw. In certain examples, the drill guide 320 may include external threads. The drill guide 320 may include a proximal end 322, a distal end 324, and a length extending from the proximal end 322 to the distal end 324.

The drill guide 320 may include a channel 326. The channel 326 may extend through the drill guide 320. The channel 326 may extend from the drill guide proximal end 322 to the drill guide distal end 324. The drill guide channel 326 may be configured to allow passage of a drill pin, which may also be referred to as a guidewire, through the drill guide 320. For example, the channel 326 may be configured to allow passage of a drill pin through the drill guide 320, which may allow a surgeon to drill a tunnel into a patient's bone, such as a patient's tibia 100. The channel 326 may be configured to allow passage of a drill pin having an outer diameter of about 0.5 mm to 8 mm, 1 mm to 6 mm, 2 mm to 4 mm, 2 mm to 3 mm or about 2.5 mm such as about 2.4 mm. For example, the channel 326 may have a diameter that is slightly larger than the drill pin such as about 0.6 mm to 8.1 mm, about 1.1 mm to 6.1 mm, about 2.1 mm to 4.1 mm, about 2.2 mm to 3.1 mm, or about 2.5 mm or about 2.6 mm, or just slightly larger than about 2.4 mm. In certain examples, the channel 326 may be configured to allow passage of a drill pin having an outer diameter of about 2.4 mm to about 2.9 mm. For example, the channel may be configured to allow passage of a pin having an outer diameter of about 2.6 mm to about 2.7 mm. In such examples, the diameter of the channel 326 may be larger than the outer diameter of the drill pin.

Figure 5A:
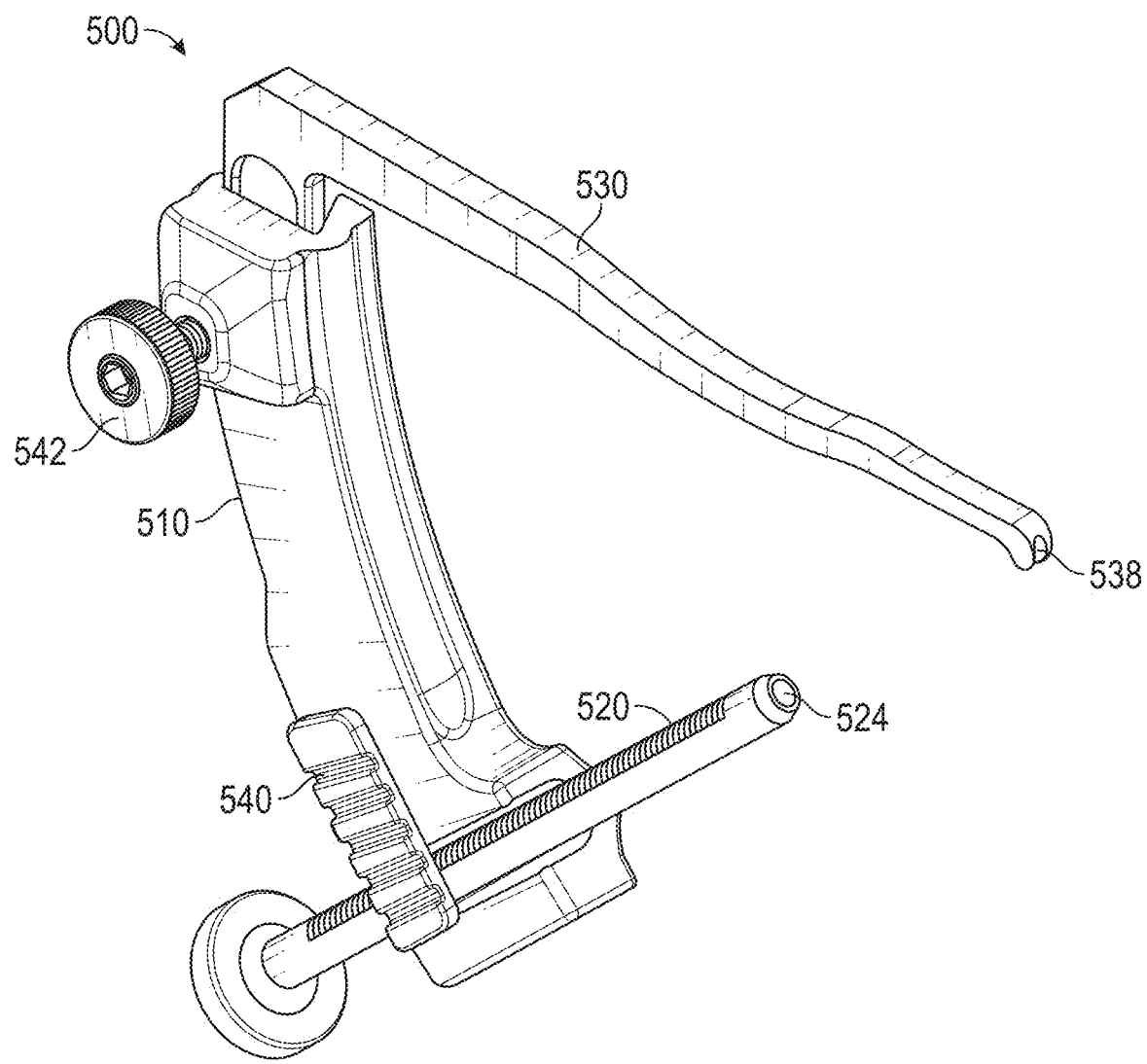
FIG. 5A illustrates a perspective view of an embodiment of a meniscal root repair guide.
Figure 5B:
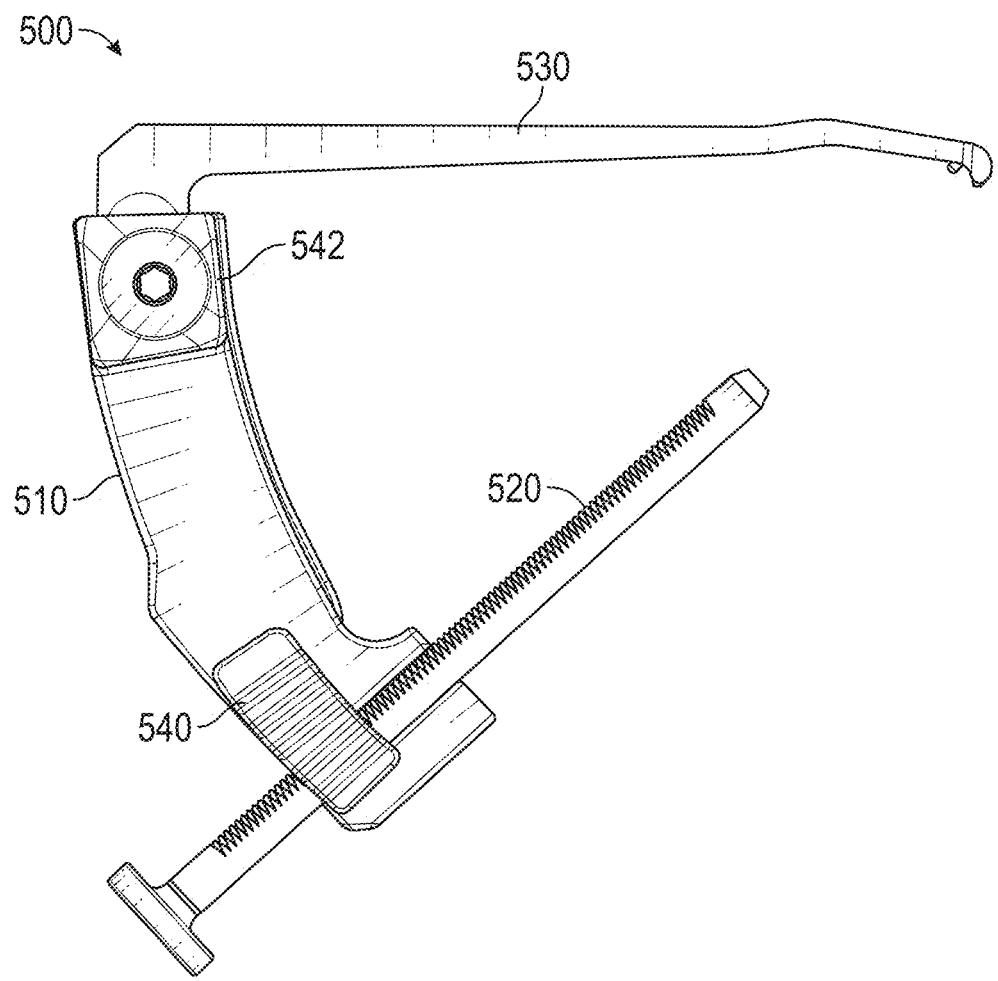
FIG. 5B illustrates a side view of the embodiment of a meniscal root repair guide shown in FIG. 5A.
Figure 5C:
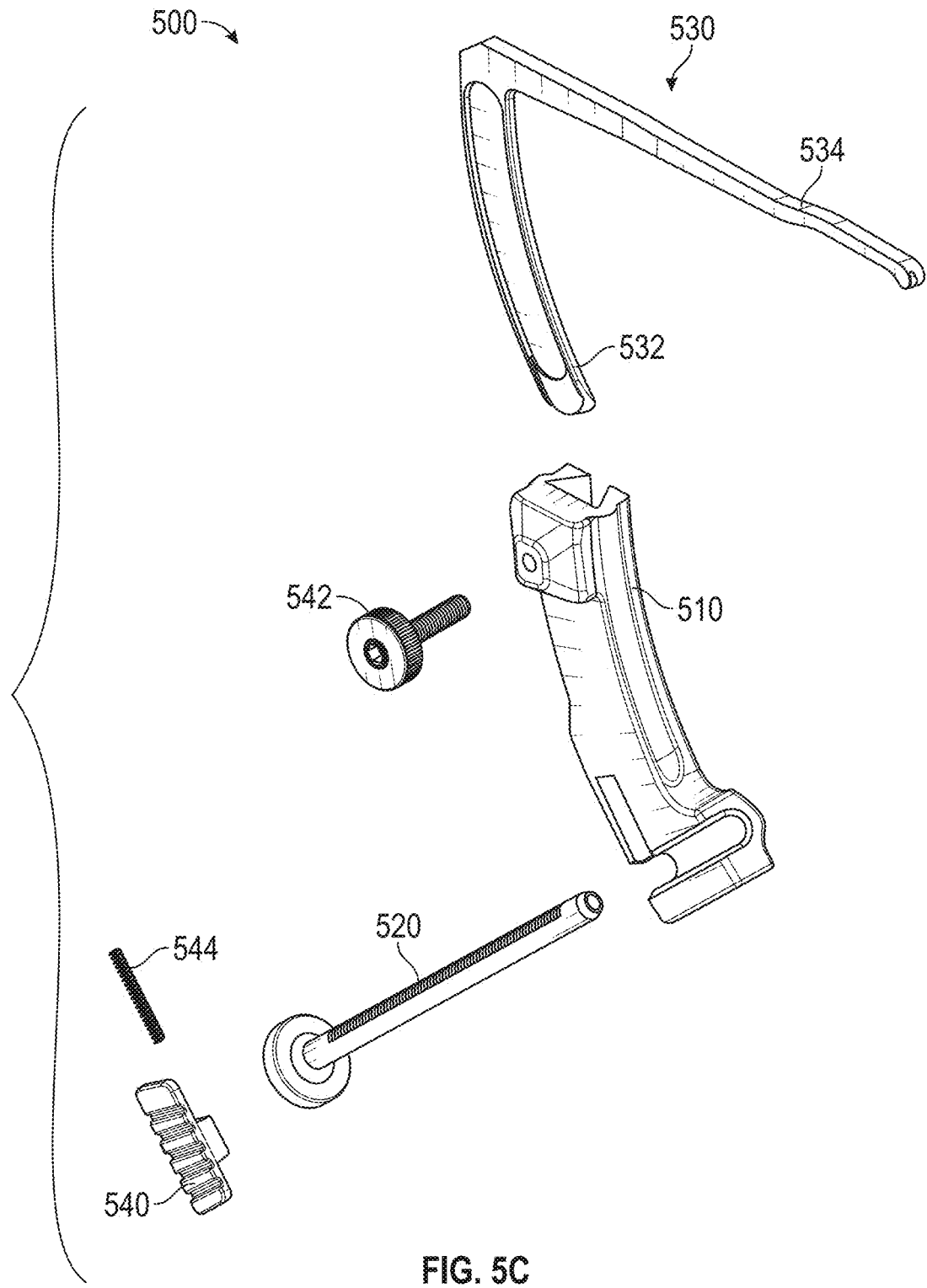
FIG. 5C illustrates an exploded view of the embodiment of the meniscal root repair guide shown in FIG. 5A.

FIGS. 5A-5C illustrate another embodiment of a meniscal root repair guide 500. The repair guide 500 may include a guide handle 510, a drill guide 520, and a meniscal guide member 530. The meniscal guide member 530 may also be referred to as a reference member 530. The repair guide 500 may also include a drill guide securement feature 540 and a reference member securement feature 542.

The drill guide securement feature 540 may also be referred to as a ratcheting component, a release slide, or a securement slide. When the drill guide securement feature 540 is in an open, or down, position, the drill guide 520 may be permitted to move freely or loosely in an axially direction within the guide handle 510. For example, when the drill guide securement feature 540 is in an open position, a surgeon may advance the drill guide 520 into a patient's tissue, as further discussed below. The drill guide securement feature 540 may use a spring 544 to secure the drill guide 520.

Positioning the drill guide securement feature 540 in a closed, or up, position may cause the drill guide 520 to be axially fixed relative to the guide handle 510. When the drill guide securement feature 540 is in the closed position, the drill guide 520 may not move axially relative to the guide handle.

In the closed position, the drill guide securement feature 540 may engage notches, grooves, detents, or other engagement features of the drill guide 520 in order to secure the drill guide 520 relative to the guide handle 510. In some examples, one side of the drill guide 520 may comprise notches, grooves, detents, or other engagement features, and the other side of the drill guide 520 may be substantially smooth. This may advantageously facilitate smooth insertion and removal of the drill guide 520 while also permitting engagement of the drill guide 520 with the drill guide securement feature 540. In certain examples, the drill guide 520 may comprise notches, grooves, detents, or other engagement features on all sides of the drill guide 520. In some examples, the drill guide 520 may comprise notches, grooves, detents, or other engagement features along the entire length of the drill guide 520. In certain examples, the drill guide 520 may comprise notches, grooves, detents, or other engagement features along a portion of the drill guide 520. A sliding drill guide securement feature 542 may advantageously allow a surgeon to quickly secure and/or release the drill guide 520 relative to the guide handle 510.

Meniscal Root Repair Kit

Figure 6:
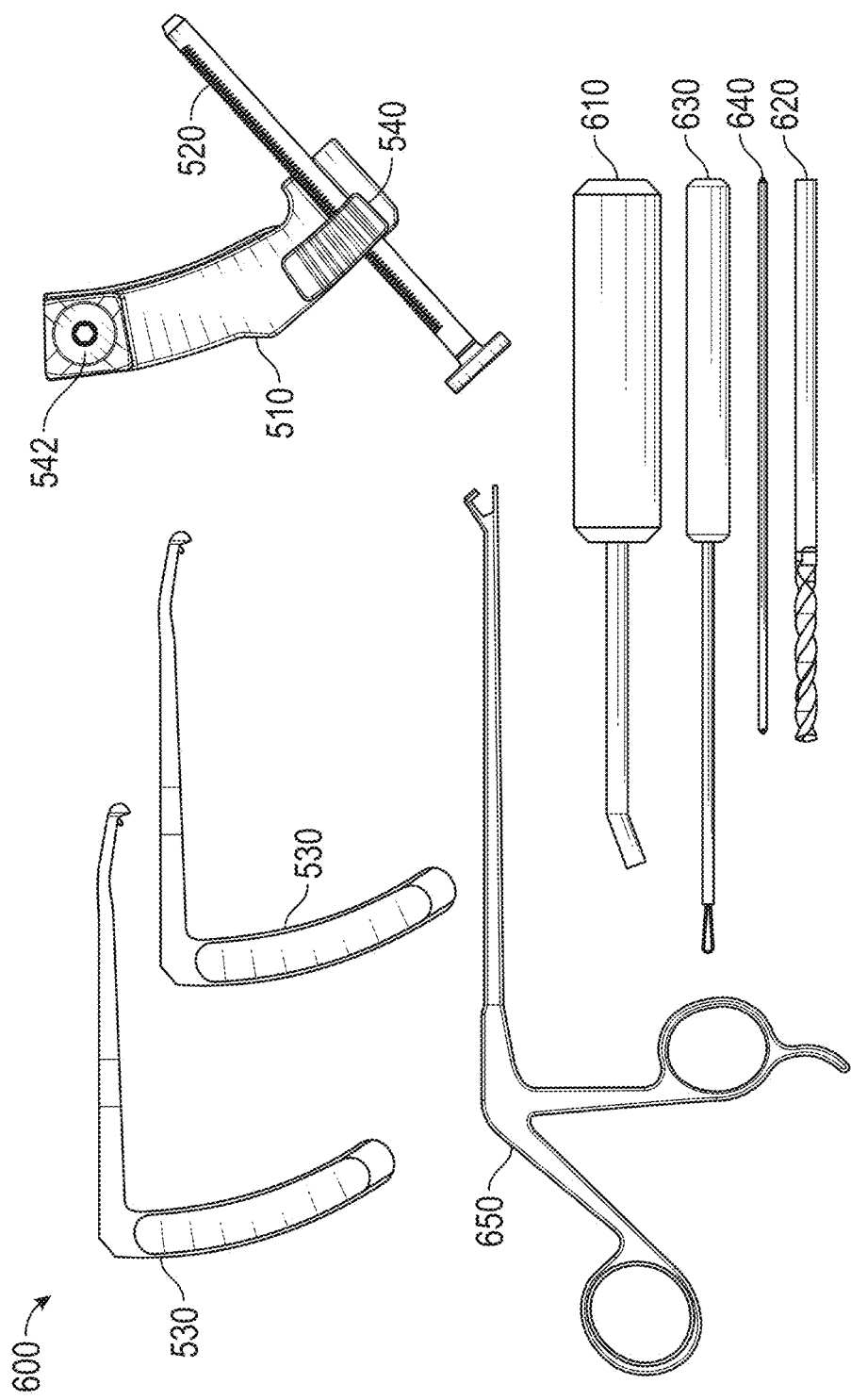
FIG. 6 illustrates an embodiment of a meniscal root repair kit.

FIG. 6 illustrates a meniscal root repair kit 600. The repair kit 600 may be used to help facilitate a meniscal root repair. The kit 600 may include a meniscal root repair guide 500 having a handle 510, a drill guide 520, a reference member 530, and securement features 540 and 542. The kit 600 may include a righthand reference member 530, a lefthand reference member 530, or both a righthand and a lefthand reference member 530. A lefthand reference member 530 may be sized and shaped to substantially align with the contour of a left tibial spine. A righthand reference member 530 may be sized and shaped to substantially align with the contour of a right tibial spine.

The kit 600 may also include a curette 610. The curette 610 may be configured to remove tissue from the surgical site. For example, the curette 610 may be configured to remove cartilage from the surgical site. The curette 610 may be used to remove cartilage from the surgical site in preparation for a meniscal root repair.

The kit 600 may also include a drill pin 620. The drill pin 620 may be configured to create a tunnel in a patient's bone. For example, the drill pin 620 may be configured to create a tunnel in a patient's tibia 100, which may allow passage of suture, wire, or other method of fixation through the tunnel to the site of repair. The drill pin 620 may be configured to pass through a channel of the drill guide 520. For example, the drill pin 620 may be sized such that it can pass through the channel of the drill guide 520. The drill pin 620 may have an axial length that is longer than an axial length of the drill guide 520. In some examples, the drill pin 620 may have an axial length of 100 mm, about 100 mm, or greater than 100 mm. In some examples, the drill pin 620 may have an axial length of about 100 mm to about 180 mm. The drill pin 620 may have an outer diameter that is smaller than the diameter of the channel of the drill guide 520. In some examples, the drill pin 620 may have an outer diameter of 2.4 mm or about 2.4 mm. In certain examples, the drill pin 620 may have an outer diameter of about 2.4 mm to about 2.9 mm.

The kit 600 may also include a cannulated drill bit 630. The cannulated drill bit 630 may include a proximal end, a distal end, and a channel extending from the proximal end to the distal end. The channel of the cannulated drill bit 630 may be configured to surround the outer diameter of the drill pin 620. The channel of the cannulated drill bit 630 may have a diameter that is slightly larger than the outer diameter of the drill pin 620. The channel of the cannulated drill bit 630 may be configured to allow passage of suture or wire through the channel.

The kit 600 may also include a delivery device 640 configured to deliver one or more sutures, wires, or other fixation components to the site of repair. The delivery device 640 may comprise a suture passer. A surgeon may operate the delivery device 640 in repairing a meniscus. For example, a surgeon may operate the delivery device 640 in repairing or reattaching a torn or otherwise damaged meniscal root. The delivery device 640 may be sized such that the delivery device 640 can pass through the channel of the cannulated drill bit 630. For example, the delivery device 640 may have an outer diameter that is smaller than the diameter of the channel of the cannulated drill bit 630.

The kit 600 may also include a clamp 650 configured to hold materials together or back during the medical procedure. The clamp 650 can be a c-clamp. The clamp 650 may be configured to hold tissue away from the surgical site. For example, the clamp 650 may be configured to hold cartilage away from the surgical site. The clamp 650 may be used to hold cartilage away from the surgical site in preparation for a meniscal root repair.

Figure 7A:
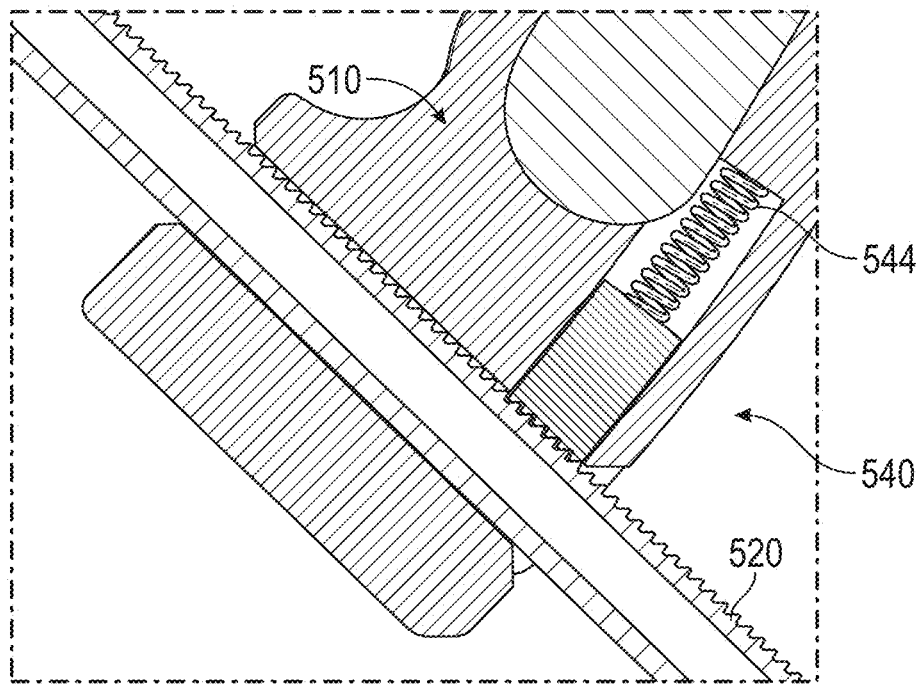
FIG. 7A illustrates the ratchet mechanism engaged.

FIG. 7A illustrates the ratchet mechanism engaged. The spring 544 allows the drill guide securement feature 540 to secure the drill guide 520. The ratchet mechanism is engaged when the notches, grooves, detents, or other engagement features of the drill guide 520 contact the notches, grooves, detents, or other engagement features of the drill guide securement feature 540.

Figure 7B:
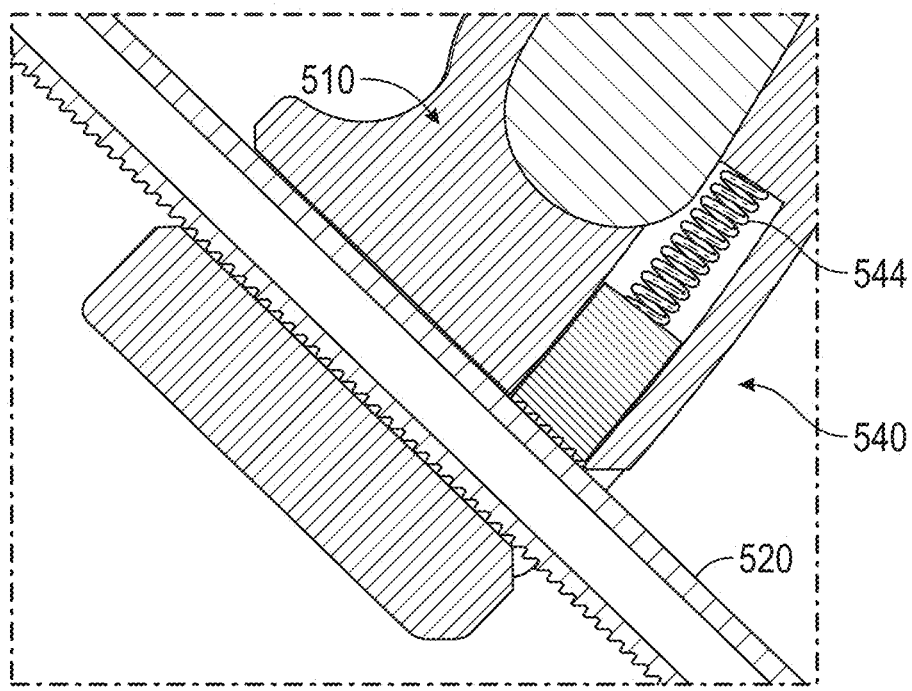
FIG. 7B illustrates the ratchet mechanism disengaged.

FIG. 7B illustrates the ratchet mechanism disengaged. The spring 544 allows the drill guide securement feature 540 to secure the drill guide 520. The ratchet mechanism is disengaged when the notches, grooves, detents, or other engagement features of the drill guide 520 do not contact the notches, grooves, detents, or other engagement features of the drill guide securement feature 540.

Figure 8A:
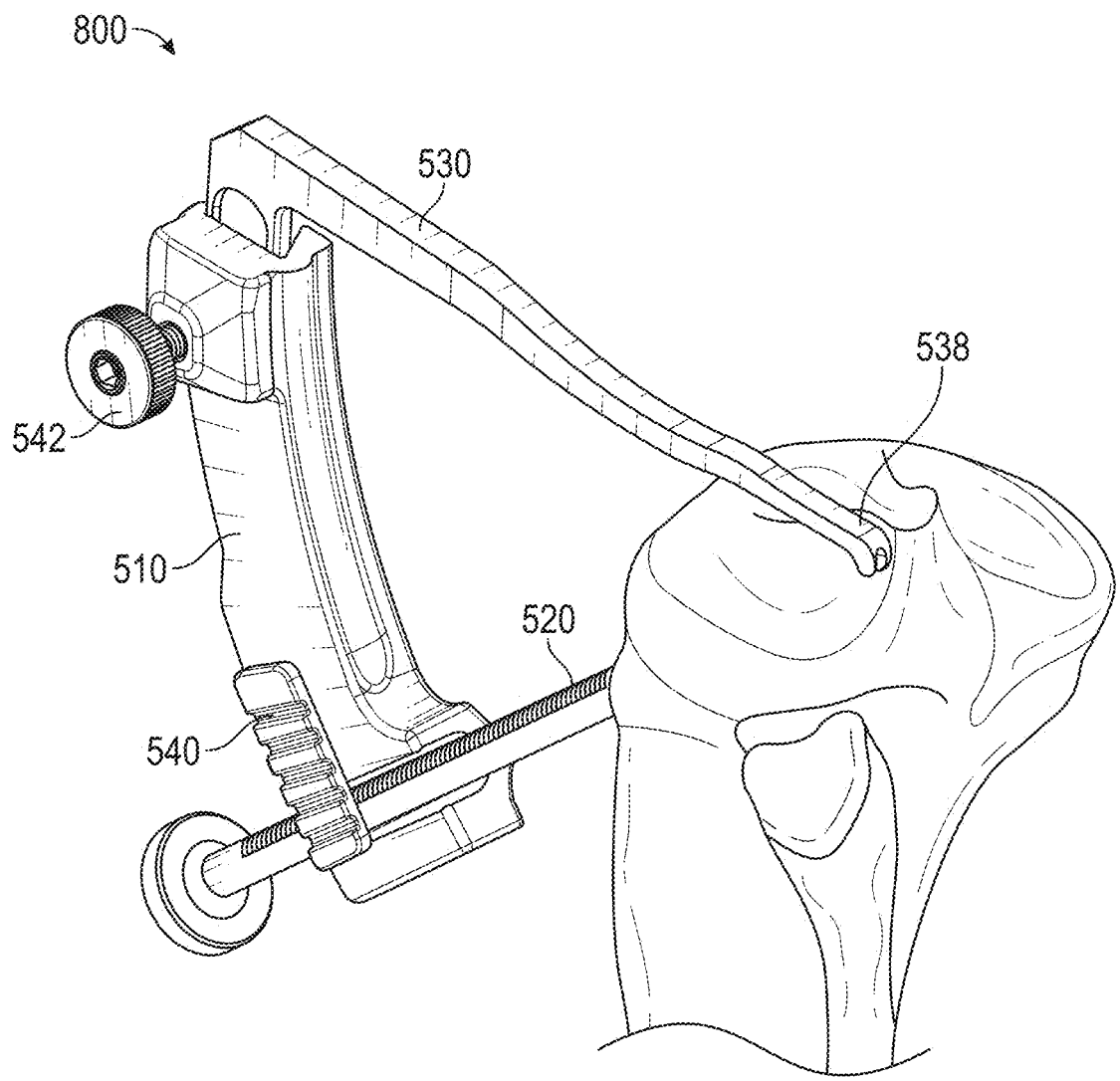
FIG. 8A illustrates a perspective view of an embodiment of a meniscal root repair guide on a patient's bone.

FIG. 8A illustrates a perspective view of an embodiment of a meniscal root repair guide on a patient's bone. The drill guide 520 and guide assistance feature 538 are engaged with the patient's anatomical feature. In this embodiment, the patient's anatomical feature is a bone.

Figure 8B:
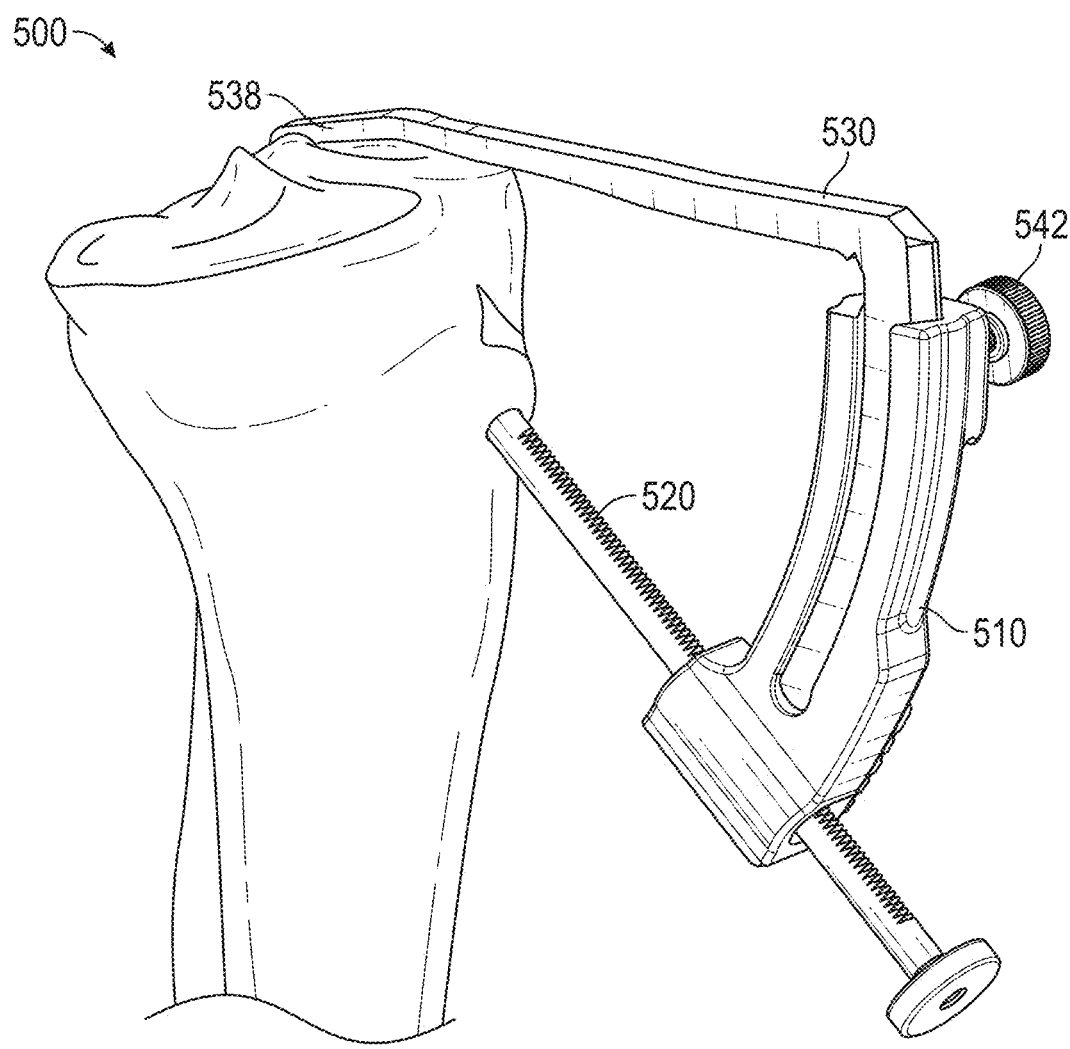
FIG. 8B illustrates a perspective view of an embodiment of a meniscal root repair guide on a patient's bone.

FIG. 8B illustrates a perspective view of an embodiment of a meniscal root repair guide on a patient's bone. The drill guide 520 and guide assistance feature 538 are engaged with the patient's anatomical feature. In this embodiment, the patient's anatomical feature is a bone.

Method of Repairing a Meniscal Root

The above-described features of the meniscal root repair guide 300, 500, 900 can help guide and properly align meniscal root repair procedures. An example method of repairing a meniscal root is described with further reference to FIGS. 1-6.

A surgeon may make a small incision in the patient's skin near the surgical site. The site of the meniscus tear may then be visually evaluated using a probe or rasp. Cartilage may then be removed from the location of repair. After the site of the meniscus tear has been evaluated and prepared for repair, a meniscus root repair guide 300 may be used to help facilitate the meniscal root repair. In certain examples, the meniscal root repair guide 500 can be placed at the anatomic footprint of the root. The meniscal root repair guide 500 can be used to ensure the drill guide 520 will exit at the footprint of the meniscus root anatomy. In some examples, the drill guide 500 is the 2.4 mm drill guide or any other suitable drill guide such as those disclosed herein.

A meniscal repair guide 500 may be provided. The repair guide 500 may be in a first configuration, which may also be referred to as a retracted configuration. In the first configuration, the guide handle 510 may engage the reference member 530. A reference member securement feature 542 may provide for secure engagement of the handle 510 and the reference member 530. For example, reference member securement feature 542 may comprise a thumbscrew which may be operated to apply a compressive force to the reference member 530 and guide handle 510.

In the first configuration, a drill guide 520 may be in a retracted state. In its retracted state, the distal end 524 of the drill guide 520 may be positioned within the guide handle 510. In certain examples, in its retracted stated, the distal end 524 of the drill guide 520 may protrude just slightly from the guide handle 510. Alternatively, in the first configuration, the drill guide 320 may not yet engage the guide handle 510.

With the repair guide 500 in its first configuration, the reference member 530 may be inserted into the patient. For example, the second arm 534 of the reference member 530 may be inserted into the patient through an incision in the patient's skin. The reference member 530 may be positioned such that it engages an anatomical feature of the patient. For example, the reference member 530 may be positioned such that it engages the patient's tibia 100, or the tibial plateau 102 of the patient's tibia 100. The reference member 530 may be positioned such that the guide assistance feature 538 engages an anatomical feature of the patient, such as the patient's tibia.

With the reference member 530 positioned such that it engages an anatomical feature of the patient, the drill guide 520 may then be advanced distally to an extended state. In advancing the drill guide 520 to its extended state, the drill guide 520 may be inserted into the patient. For example, the drill guide 520 may be inserted into the patient through an incision in the patient's skin. In certain examples, the drill guide 320 may be advanced using a pushing motion, a screwing motion, or a combination of pushing and screwing motions.

With the drill guide 520 advanced to its extended state, a drill guide securement feature 540 may provide for secure engagement of the handle 510 and the drill guide 520. For example, drill guide securement feature 540 may comprise a ratcheting component, which may also be referred to as a release slide or a securement slide, configured to engage drill guide 520. Alternatively, as previously discussed, drill guide securement feature 540 may comprise a thumbscrew which may be operated to apply a compressive force to the drill guide 520 and handle 510.

With the drill guide 520 in its extended, or deployed, configuration, a drill pin 620 may then be advanced through the channel of the drill guide 520. In some examples, a drill pin 620 having an outer diameter of 2.4 mm or about 2.4 mm (such as described herein) may be advanced through the channel of the drill guide 520. In certain examples, the drill pin 620 may have an outer diameter of about 2.4 mm to about 2.9 mm (such as described herein). In some examples, the drill pin 620 may be operated to form a tunnel in the patient's tibia. Such a tunnel in the patient's tibia may allow for passage of suture, wire, or other method of fixation.

With the drill pin 620 inserted into the patient's tibia, the surgeon may remove the drill guide 520 and the reference member 530 from the patient. A cannulated drill bit 630 may then be advanced over the drill pin 620. With the cannulated drill bit 630 advanced to the site of repair, the drill pin 620 may then be removed from the patient.

In certain examples, the drill pin 620 and the cannulated drill bit 630 may be advanced simultaneously into the patient. The drill pin 620 may be positioned within the channel of the cannulated drill bit 630, such that the drill pin 620 and the cannulated drill bit 630 are concentric with each other when inserted into the patient. The drill pin 620 and the cannulated drill bit 630 may be advanced through the channel of the drill guide 520.

A surgeon may then pass suture, wire, or another method of fixation through the channel of the cannulated drill bit 630 and to repair the meniscus tear. A surgeon may pass the suture, wire, or other method of fixation via a delivery device 640. The meniscus may be repaired with a button, anchor, or other method of fixation.

Figure 9A:
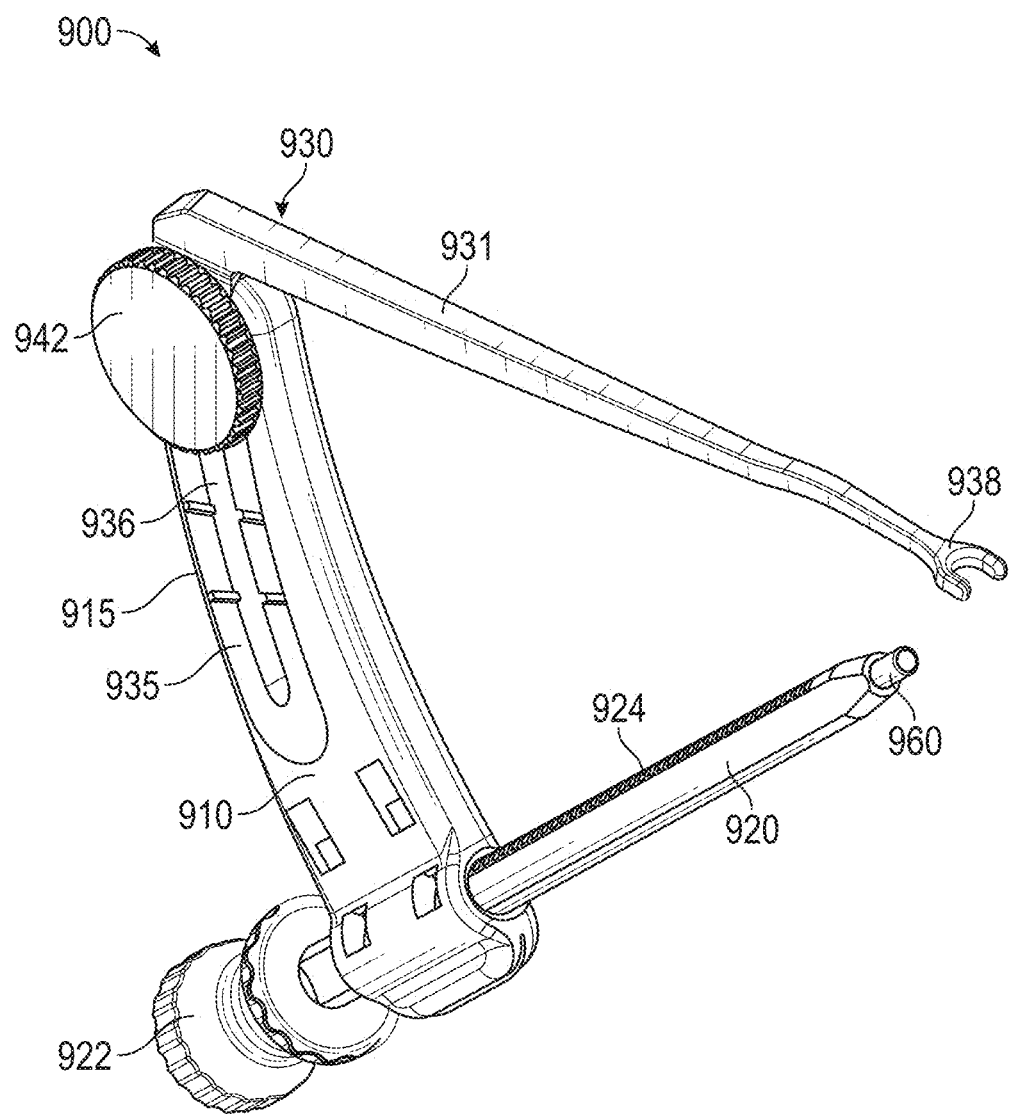
FIG. 9A is a perspective view of another example of a meniscus repair guide.
Figure 9B:
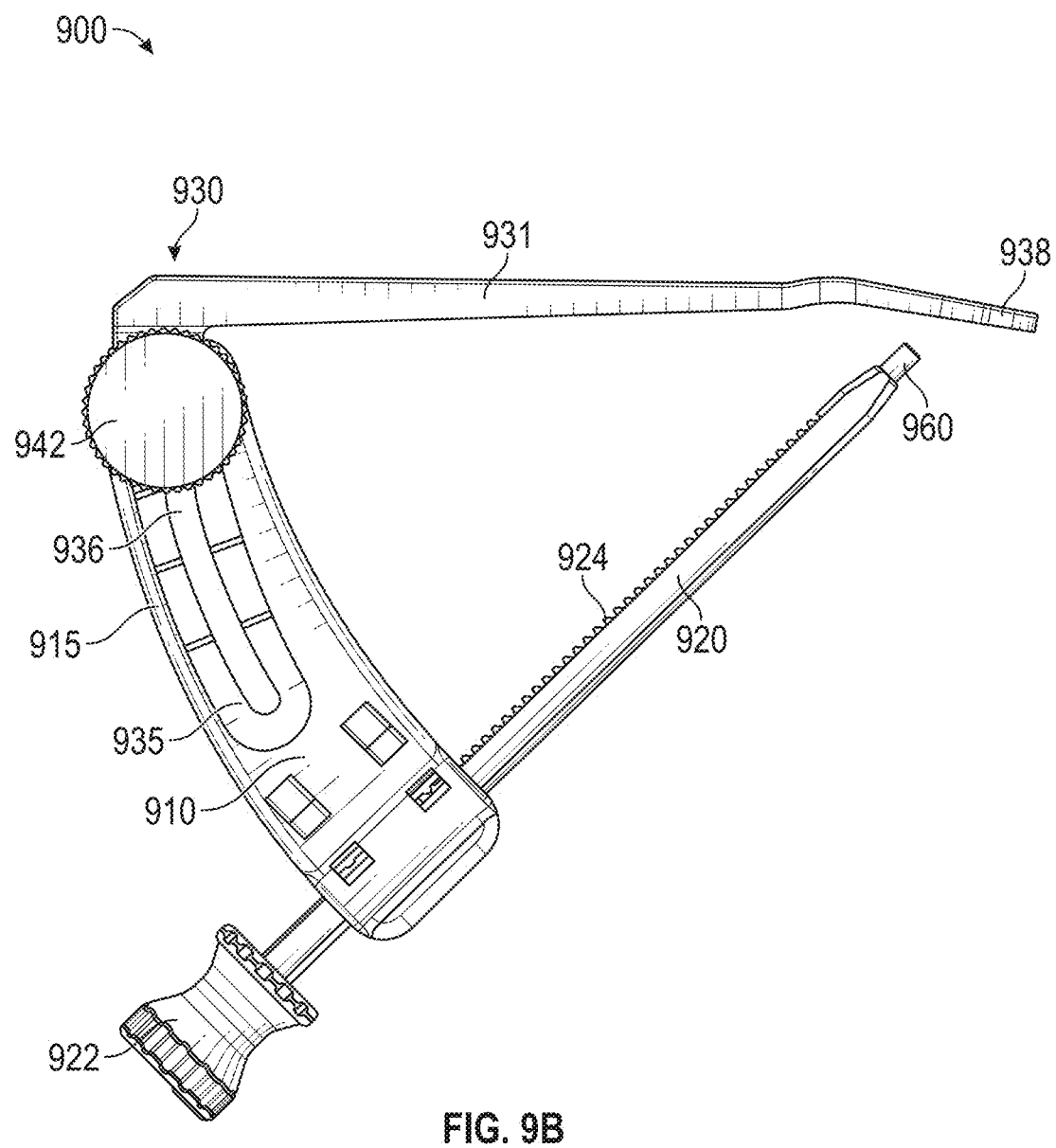
FIG. 9B is a side view of the example of the meniscus repair guide of FIG. 9A.
Figure 9C:
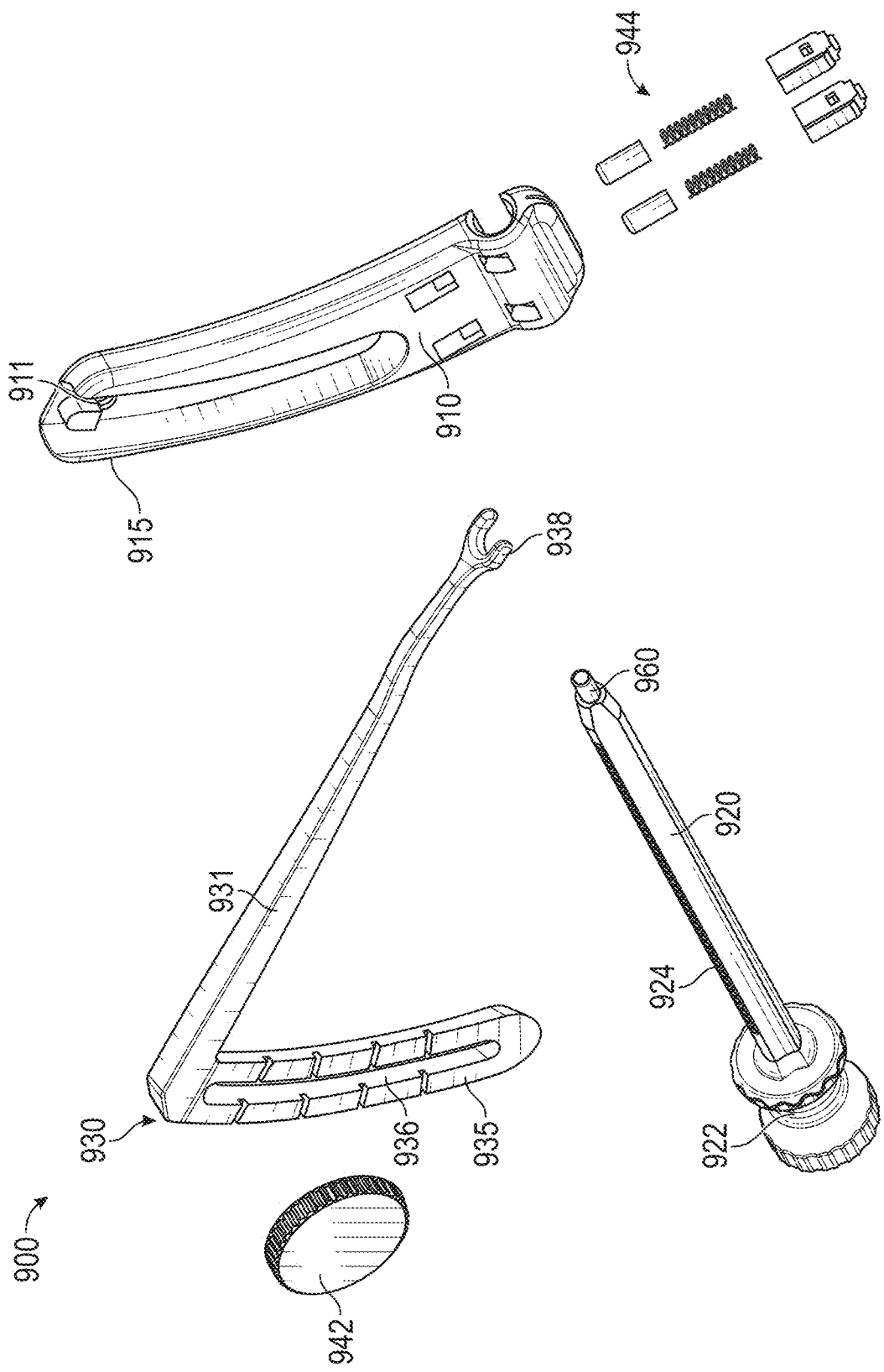
FIG. 9C is an exploded view of the example of the meniscus repair guide of FIG. 9A.
Figure 9D:
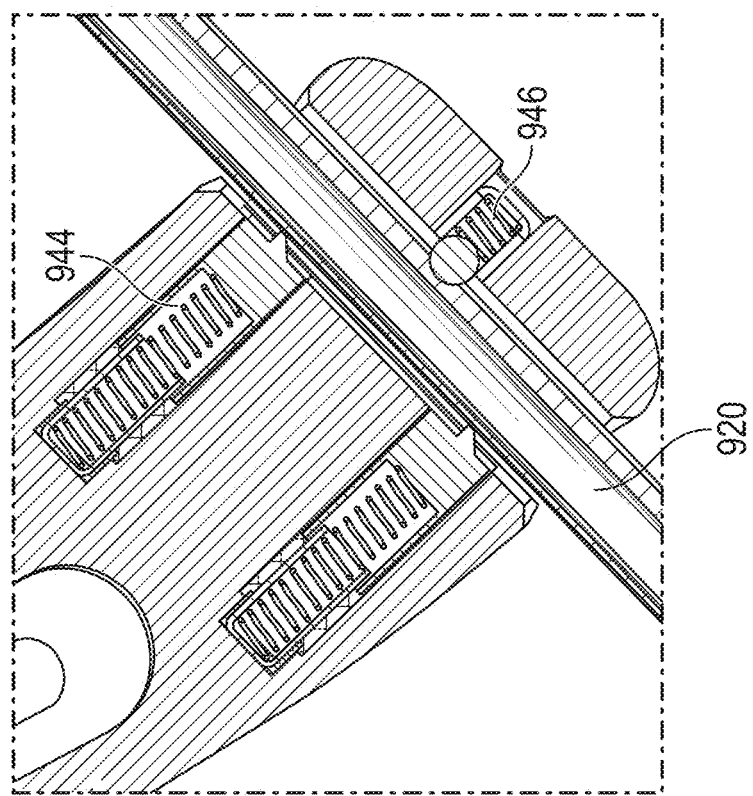
FIG. 9D is a zoomed in view of an engaged ratcheting mechanism of the example of the meniscus repair guide of FIG. 9A.
Figure 9E:
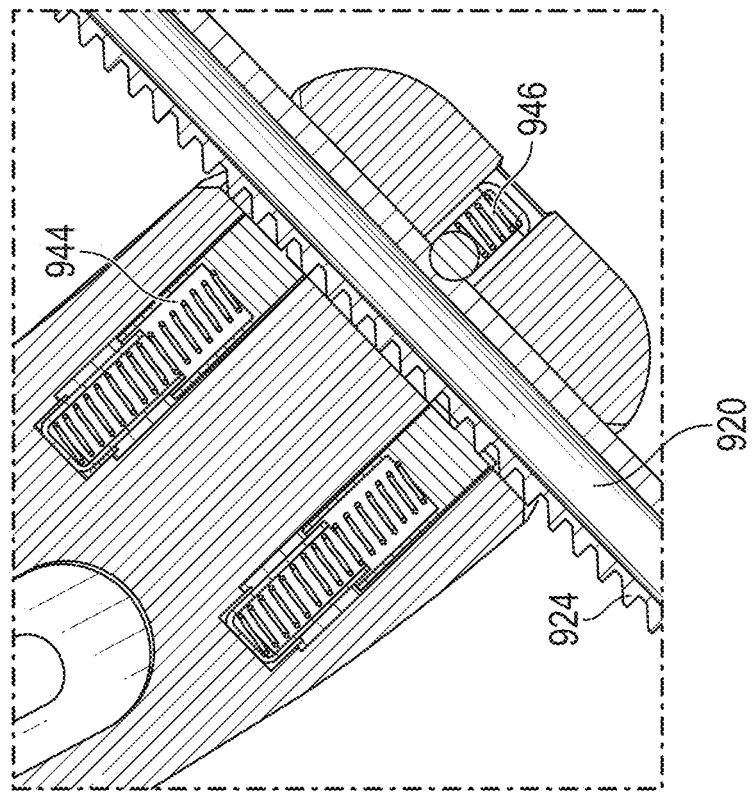
FIG. 9E is a zoomed in view of a disengaged ratcheting mechanism of the example of the meniscus repair guide of FIG. 9A.
Figure 9F:
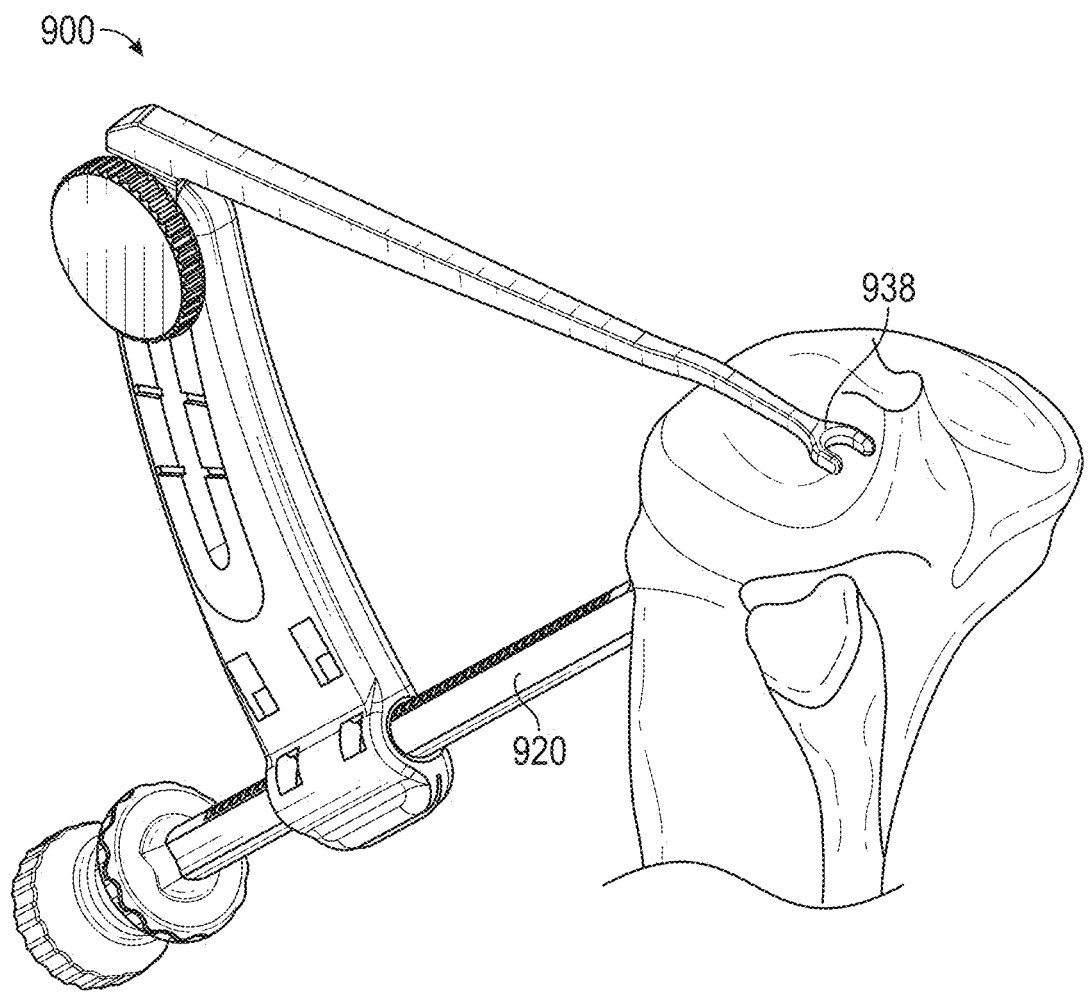
FIG. 9F is a perspective view of the example of the meniscus repair guide of FIG. 9A engaging a bone.
Figure 9G:
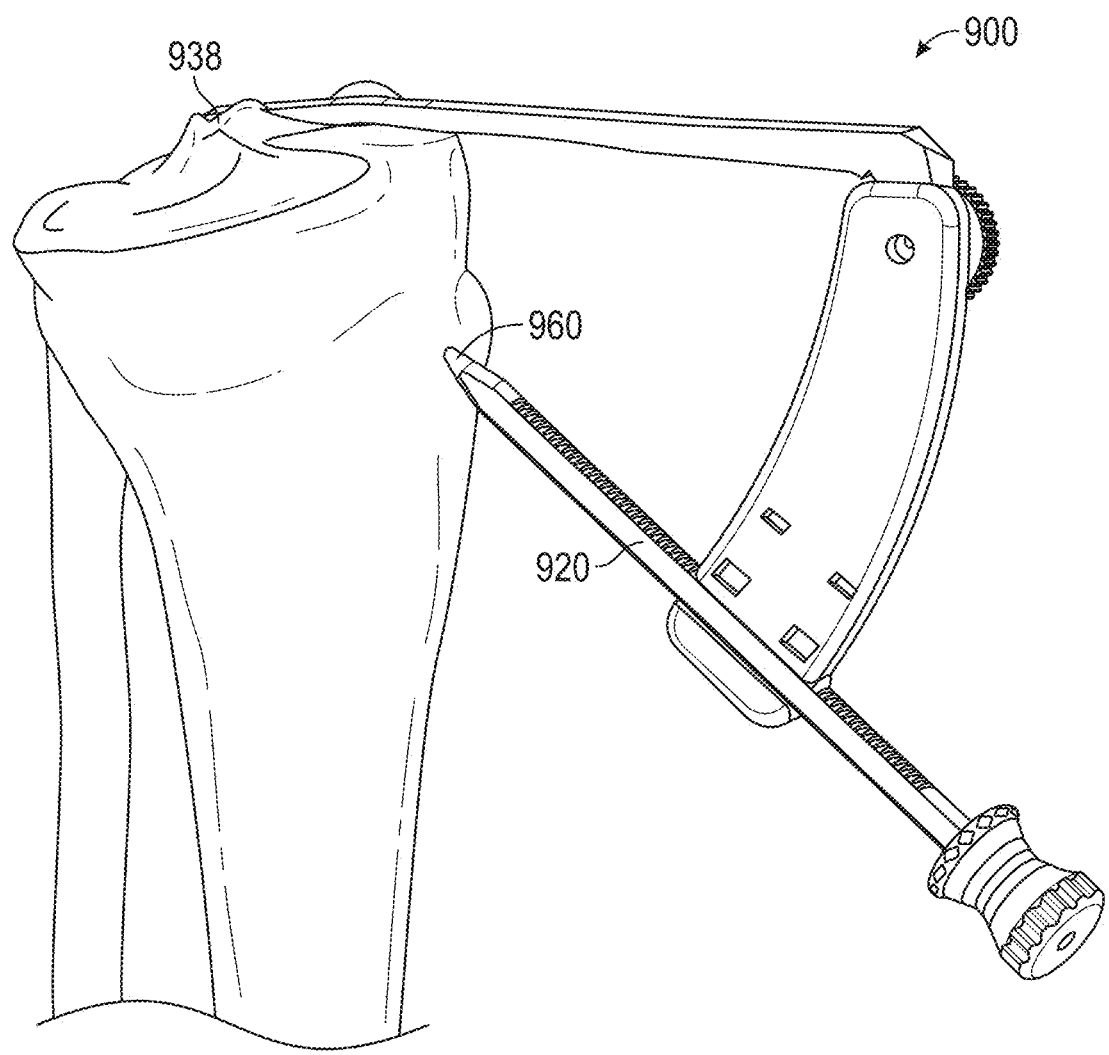
FIG. 9G is a side view of the example of the meniscus repair guide of FIG. 9A engaging a bone.

FIG. 9A is a perspective view of another example of a meniscus repair guide 900. FIG. 9B is a side view of the example of the meniscus repair guide 900 of FIG. 9A. FIG. 9C is an exploded view of the example of the meniscus repair guide 900 of FIG. 9A. FIG. 9D is a zoomed in view of an engaged ratcheting mechanism of the example of the meniscus repair guide 900 of FIG. 9A. FIG. 9E is a zoomed in view of a disengaged ratcheting mechanism of the example of the meniscus repair guide 900 of FIG. 9A. FIG. 9F is a perspective view of the example of the meniscus repair guide 900 of FIG. 9A engaging a bone. FIG. 9G is a side view of the example of the meniscus repair guide 900 of FIG. 9A engaging a bone.

The meniscus guide 900 can be similar to the meniscus guides 300, 500 described herein. The meniscus guide 900 can include a knob 942 that allows the reference member 930, or guide member, to be adjusted along the handle 910. The reference member 930 can be moveable with respect to the handle 910. A dial, switch, or other component may be used to move the reference member 930.

The knob 942 can be rotated to adjust the position of the reference member 930 along the handle 910. The reference member 930 can include two arms forming an angle. The reference member 930 can include a first arm 935 that can fit within a cavity 915 of the handle 910. The reference member 930 can include a second arm 931 with an engagement component 938 at the distal end.

The knob 942 can include a shaft that extends through the central aperture 936 of the securement portion of the reference member 930. The shaft of the knob 942 can also extend through an aperture 911 in the handle 910. Rotating the knob 942 can adjust the first arm 935 up and down in the cavity 915. A user can adjust the reference member 930 using the knob 942 while the reference member 930 is positioned on a bone. This can adjust the angle of the drill guide 920 on the bone due to the change in position of the handle 910 relative to the reference member 930.

In some examples, the first arm 935 of the meniscus guide 900 can be visible while the user is adjusting the angle of the reference member 930. In some examples, the first arm 935 of the reference member 930 can be marked with degrees. This marking can indicate the angle between the reference member 930 and the drill guide 920 when the knob 942 is aligned with the marking. Advantageously, this can indicate to a user the angle at which they can drill into the anatomical feature.

The engagement component 938 can be used to contact an anatomical feature, for example a bone. Tools, for example sutures, that extend through the bone can be routed through the engagement component 938. The engagement component 938 of the reference member 930 can include two curved portions that extend laterally from the distal end of the guide member. The engagement component 938 can be wider than the rest of the reference member 930. The engagement component 938 can be U-shaped.

The meniscus repair guide 900 can include a drill bit 960 on the distal end of the drill guide 920. The drill bit 960 can be an elliptical drill bit. For example, the drill bit 960 can be circular or ovoid. The drill bit 960 can be malleted into the anatomical feature. Advantageously, the drill bit 960 can be sized and shaped to secure to the anatomical feature easily. For example, the circular drill bit 960 can be malleted into a tibial bone.

The drill guide 920 can include a drill guide knob 922 on the proximal end. The drill guide knob 922 can be rotated to extend and retract the drill guide 920. The drill guide knob 922 can be shaped for efficient and easy rotation by a user. The drill guide knob 922 can be cylindrical with an inwardly depressed mid-section. The diameter of the drill guide knob 922 can be smaller near the center along the longitudinal axis. A user can enact force on the drill guide knob 922 to mallet the drill bit 960 into the anatomical feature. Tools can be passed through the channel of the drill guide 920. For example, a suture can be passed through the drill guide 920 and extend into a cavity in the anatomical feature. The tools can be passed through a proximal end of the drill guide knob 922. The tools can pass through the center of the drill bit 960 along the longitudinal axis. Tools can extend through an aperture on the distal end of the drill bit 960. Once the drill guide 920 is in position, a pin, reamer, or drill bit may be used to form a tunnel in the anatomical feature, for example a patient's bone.

The meniscal repair guide 900 can include one or more sets of spring-loaded features for engaging the ratchet of the drill guide 920. The securement components can selectively lock the drill guide 920 in place relative to the handle 910. For example, the meniscal repair guide 900 can include two sets of spring-loaded features for engaging the ratchet of the drill guide 920. In some examples, the meniscal repair guide 900 can include between 3 and 10 sets of spring-loaded features for engaging the ratchet of the drill guide 920. The spring-loaded features 944 can include a ratchet, a spring, a cap, and/or a spring cup. The spring-loaded features 944 can engage grooves 924 of the drill guide 920 to secure the drill guide 920 in place. The grooves 924 of the drill guide 920 can extend longitudinally along the drill guide 920. The grooves 924 can be cut orthogonal to the centerline axis of the drill guide 920.

As shown with respect to FIGS. 9D and 9E, the drill guide 920 can be rotated to engage or disengage the grooves 924. The drill guide knob 922 can be used to rotate the drill guide 920. In some examples, the drill guide 920 can include a divot opposite the grooves 924 to receive part of a ball plunger 946.

In some examples, the meniscal repair guide 900 can include a ball plunger 946 for engaging the drill guide 920. The ball plunger 946 can engage the drill guide 920 when the ratchet mechanism is engaged. Advantageously, engaging the drill guide 920 with both the spring loaded features 944 and the ball plunger 946 can increase the stability of the drill guide 920.

Figure 10:
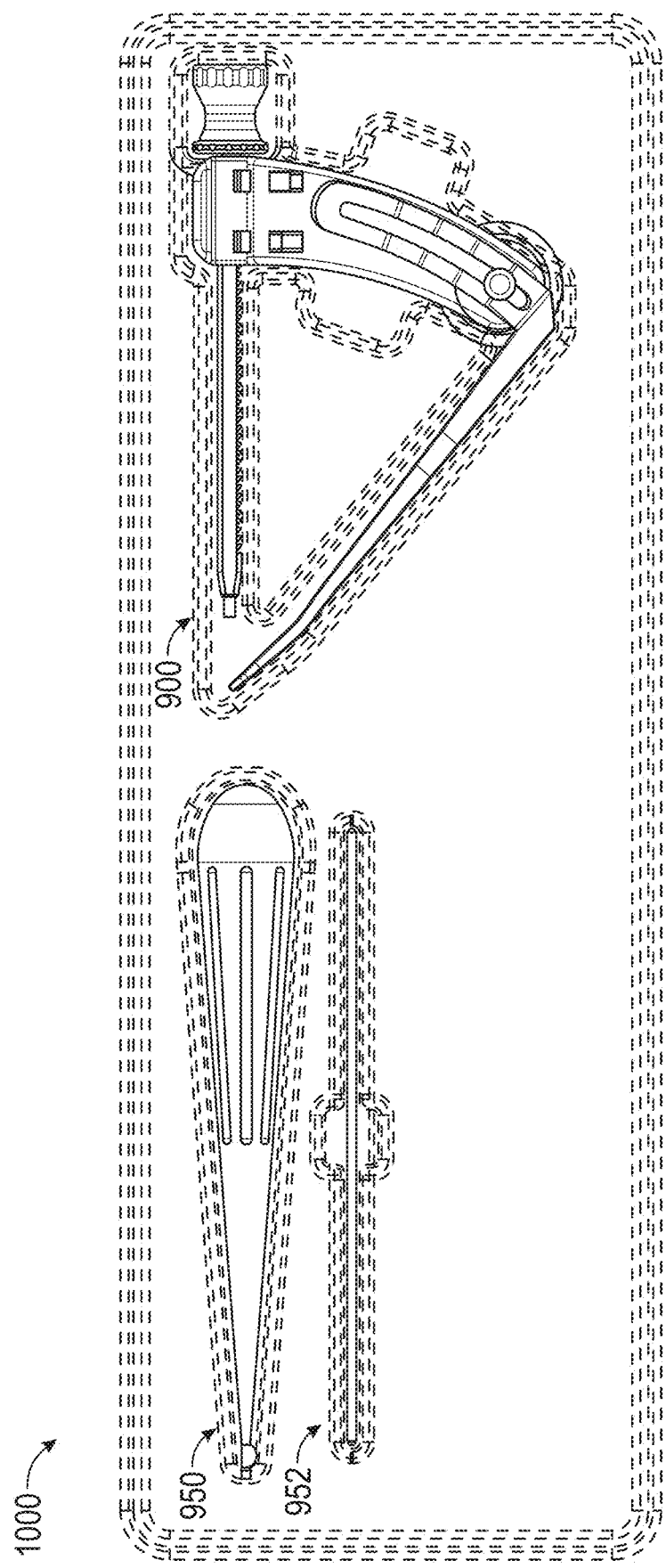
FIG. 10 shows another example of a kit for meniscal repair.

FIG. 10 shows another example of a kit 1000 for meniscal repair.

The kit 1000 can include a meniscus repair guide 900. The kit can include a cutteage 950. The kit 1000 can include a pin 952. In some examples, the pin 952 can be a 2.4 mm pin. In some examples, the pin 952 can be between 2 mm and 3 mm. In some examples, the pin 952 can be between 1 mm and 5 mm. In some examples, the kit 1000 can include a suture retriever. In some examples, the meniscus repair guide 900 can be assembled in the kit 1000. In some examples, the meniscus repair guide 900 can be disassembled in the kit 1000.

The cutteage 950 can be a curette to remove tissue by scraping and/or scooping. The pin 952 can be used in the drill guide of the meniscus repair guide 900. The meniscus repair guide 900 can have a lefthand reference member and/or a righthand reference member. In some examples, the kit 100 may include a suture button. In some examples, the kit 100 may include a clamp.

Figure 11A:
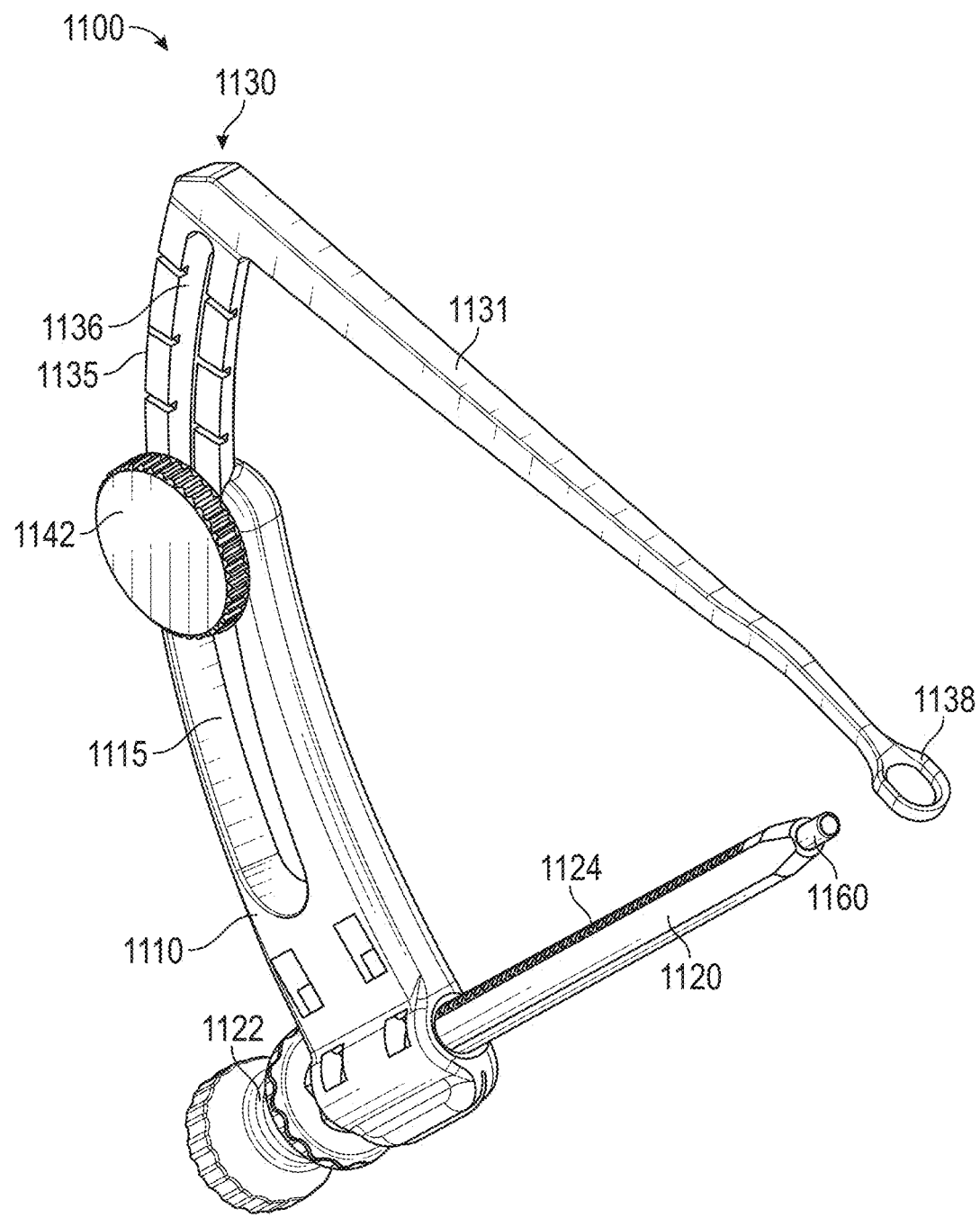
FIG. 11A is a perspective view of an example of an anterior cruciate ligament (ACL) repair guide.
Figure 11B:
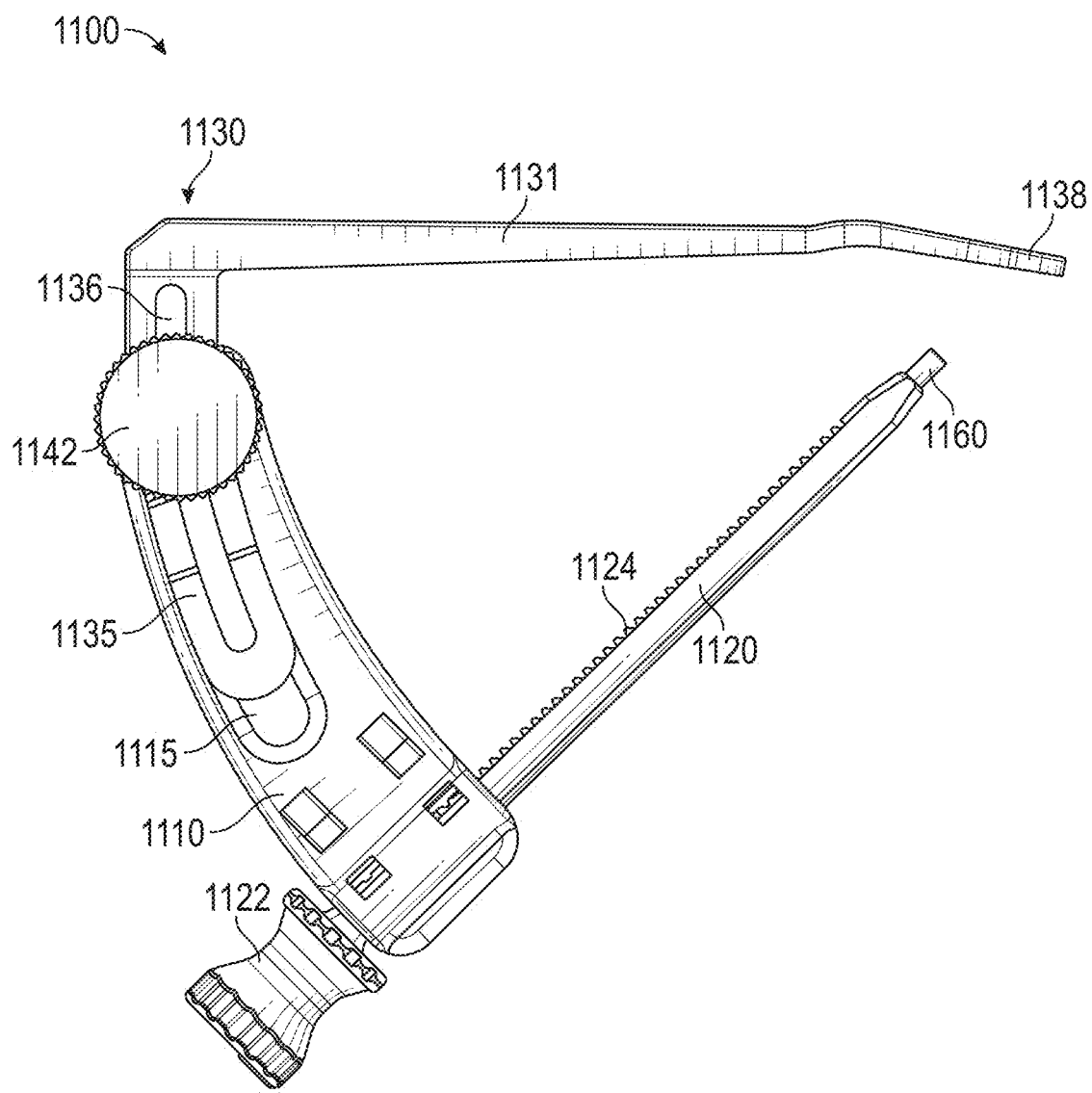
FIG. 11B is a side view of the example of the ACL repair guide of FIG. 11A.
Figure 11C:
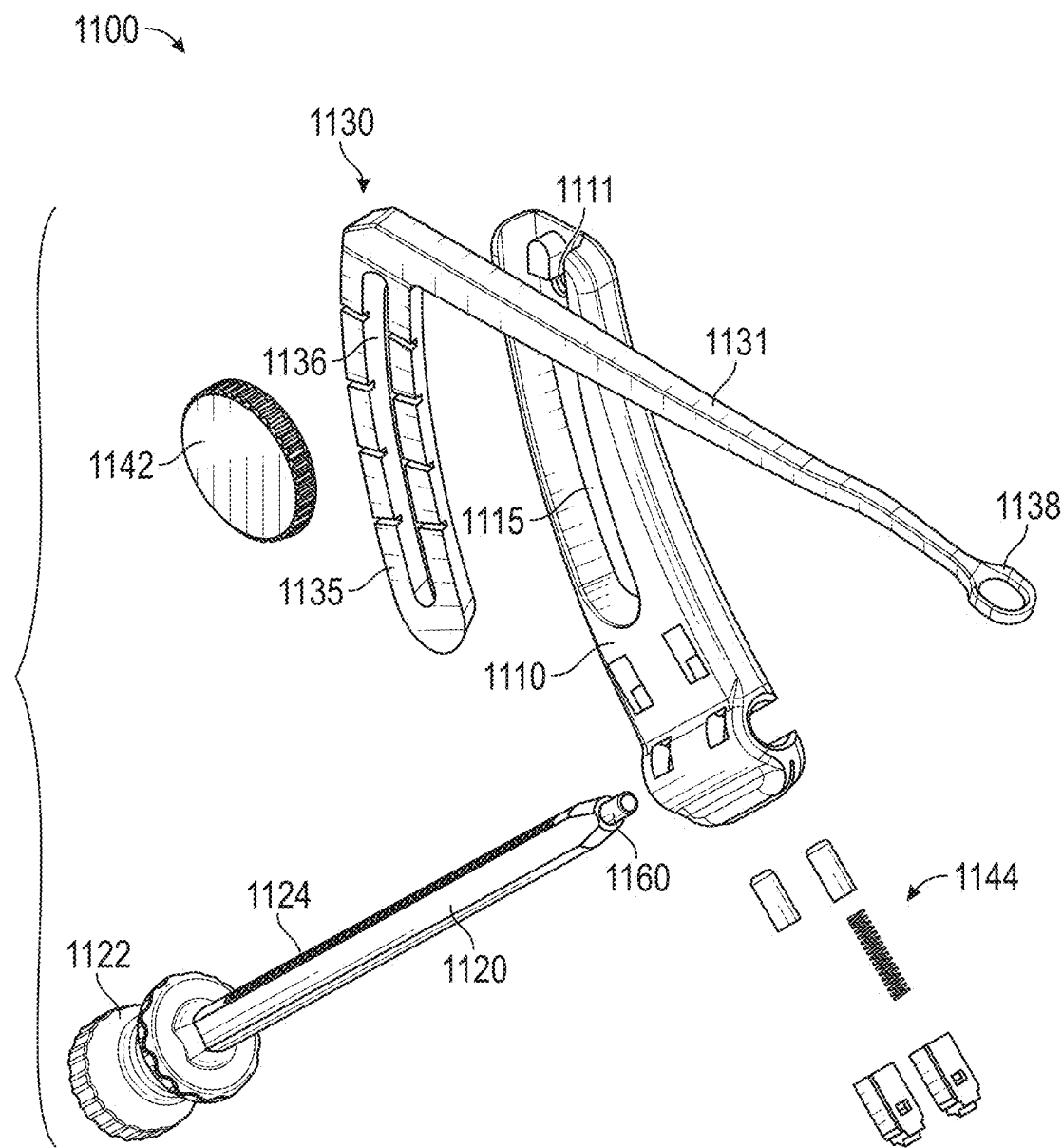
FIG. 11C is an exploded view of the example of the ACL repair guide of FIG. 11A.
Figure 11E:
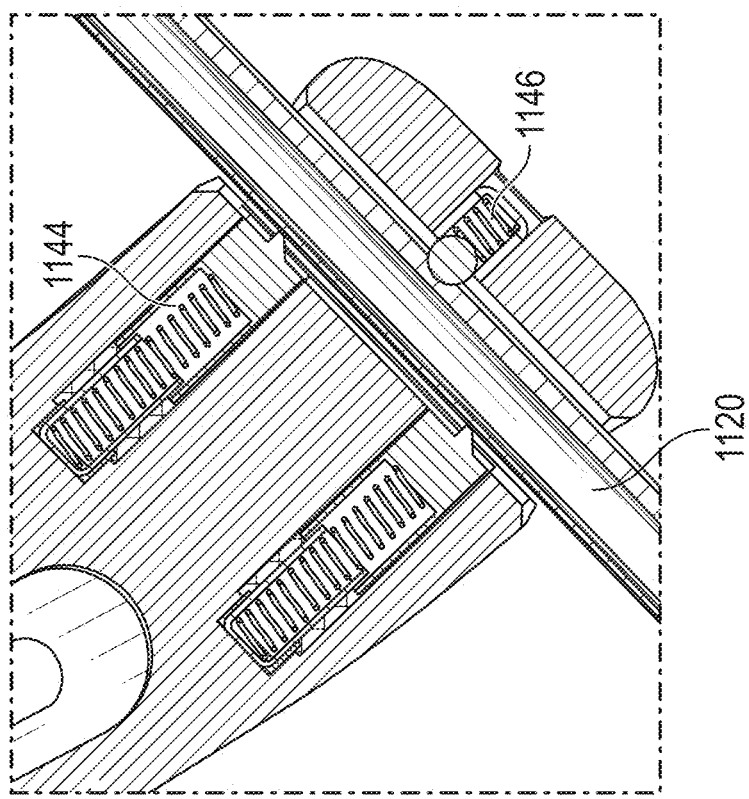
FIG. 11E is a zoomed in view of a disengaged ratcheting mechanism of the example of the ACL repair guide of FIG. 11A.
Figure 11D:
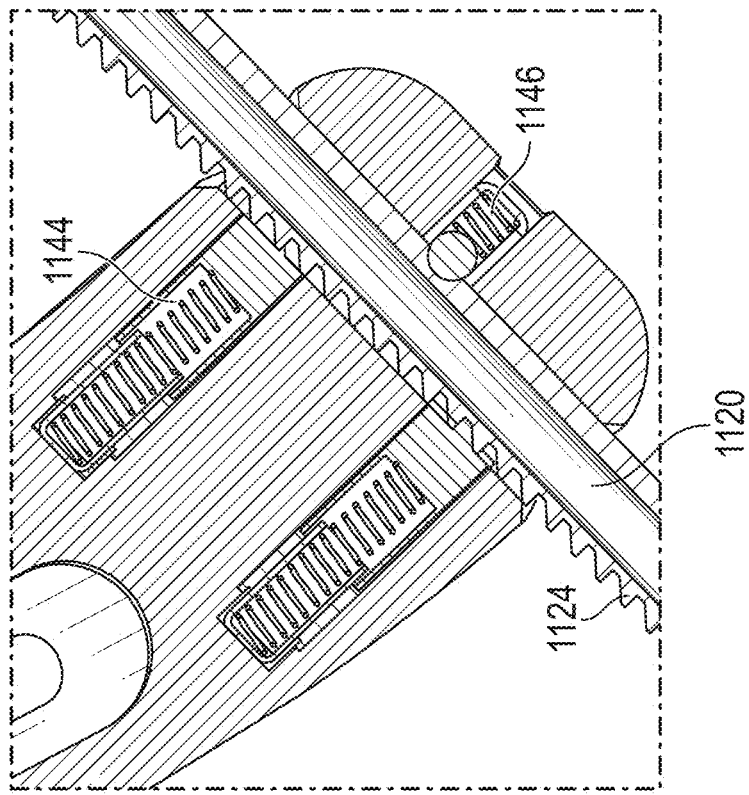
FIG. 11D is a zoomed in view of an engaged ratcheting mechanism of the example of the ACL repair guide of FIG. 11A.

FIG. 11A is a perspective view of an example of an anterior cruciate ligament (ACL) repair guide 1100. FIG. 11B is a side view of the example of the ACL repair guide 1100 of FIG. 11A. FIG. 11C is an exploded view of the example of the ACL repair guide 1100 of FIG. 11A. FIG. 11D is a zoomed in view of an engaged ratcheting mechanism of the example of the ACL repair guide 1100 of FIG. 11A. FIG. 11E is a zoomed in view of a disengaged ratcheting mechanism of the example of the ACL repair guide 1100 of FIG. 11A.

The ACL repair guide 1100 can be similar to the meniscus repair guide 900 as described with respect to FIGS. 9A-9E.

The ACL guide 1100 can be similar to the ACL guides 300, 500 described herein. The ACL guide 1100 can include a knob 1142 that allows the reference member 1130, or guide member, to be adjusted along the handle 1110.

The knob 1142 can be rotated to adjust the position of the reference member 1130 along the handle 1110. The reference member 1130 can include two arms forming an angle. The reference member 1130 can include a first arm 1135 that can fit within a cavity 1115 of the handle 1110. The reference member 1130 can include a second arm 1131 with an engagement component 1138 at the distal end.

The knob 1142 can include a shaft that extends through the central aperture 1136 of the securement portion of the reference member 1130. The shaft of the knob 1142 can also extend through an aperture 1111 in the handle 1110. Rotating the knob 1142 can adjust the first arm 1135 up and down in the cavity 1115. A user can adjust the reference member 1130 using the knob 1142 while the reference member 1130 is positioned on a bone. This can adjust the angle of the drill guide 1120 on the bone due to the change in position of the handle 1110 relative to the reference member 1130.

In some examples, the first arm 1135 of the ACL guide 1100 can be visible while the user is adjusting the angle of the reference member 1130. In some examples, the first arm 1135 of the reference member 1130 can be marked with degrees. This marking can indicate the angle between the reference member 1130 and the drill guide 1120 when the knob 1142 is aligned with the marking. Advantageously, this can indicate to a user the angle at which they can drill into the anatomical feature.

The engagement component 1138 can be used to contact an anatomical feature, for example a bone. Tools, for example sutures, that extend through the bone can be routed through the engagement component 1138. The guide member 1130 can include an engagement feature 1138 at the distal end. The engagement feature 1138 can be elliptical. For example, the engagement feature 1138 can be circular or ovoid. The circular engagement feature 1138 can surround sutures routed from the distal end of the tunnel formed in a patient's bone. In some examples, the engagement feature 1138 can be another closed shape, for example a square, a rectangle, a hexagon, an octagon, or a triangle.

The ACL repair guide 1100 can include a drill bit 1160 on the distal end of the drill guide 1120. The drill bit 1160 can be an elliptical drill bit. For example, the drill bit 1160 can be circular or ovoid. The drill bit 1160 can be malleted into the anatomical feature. Advantageously, the drill bit 1160 can be sized and shaped to secure to the anatomical feature easily. For example, the circular drill bit 1160 can be malleted into a tibial bone.

The drill guide 1120 can include a drill guide knob 1122 on the proximal end. The drill guide knob 1122 can be rotated to extend and retract the drill guide 1120. The drill guide knob 1122 can be shaped for efficient and easy rotation by a user. The drill guide knob 1122 can be cylindrical with an inwardly depressed mid-section. The diameter of the drill guide knob 1122 can be smaller near the center along the longitudinal axis. A user can enact force on the drill guide knob 1122 to mallet the drill bit 1160 into the anatomical feature. Tools can be passed through the channel of the drill guide 1120. For example, a suture can be passed through the drill guide 1120 and extend into a cavity in the anatomical feature. The tools can be passed through a proximal end of the drill guide knob 1122. The tools can pass through the center of the drill bit 1160 along the longitudinal axis. Tools can extend through an aperture on the distal end of the drill bit 1160. Once the drill guide 1120 is in position, a pin, reamer, or drill bit may be used to form a tunnel in the anatomical feature, for example a patient's bone.

The meniscal repair guide 1100 can include one or more sets of spring-loaded features for engaging the ratchet of the drill guide 1120. The securement components can selectively lock the drill guide 1120 in place relative to the handle 1110. For example, the meniscal repair guide 1100 can include two sets of spring-loaded features for engaging the ratchet of the drill guide 1120. In some examples, the meniscal repair guide 1100 can include between 3 and 10 sets of spring-loaded features for engaging the ratchet of the drill guide 1120. The spring-loaded features 1144 can include a ratchet, a spring, a cap, and/or a spring cup. The spring-loaded features 1144 can engage grooves 1124 of the drill guide 1120 to secure the drill guide 1120 in place. The grooves 1124 of the drill guide 1120 can extend longitudinally along the drill guide 1120. The grooves 1124 can be cut orthogonal to the centerline axis of the drill guide 1120.

As shown with respect to FIGS. 11D and 11E, the drill guide 1120 can be rotated to engage or disengage the grooves 1124. The drill guide knob 1122 can be used to rotate the drill guide 1120. In some examples, the drill guide 1120 can include a divot opposite the grooves 1124 to receive part of a ball plunger 1146.

In some examples, the meniscal repair guide 1100 can include a ball plunger 1146 for engaging the drill guide 1120. The ball plunger 1146 can engage the drill guide 1120 when the ratchet mechanism is engaged. Advantageously, engaging the drill guide 1120 with both the spring loaded features 1144 and the ball plunger 1146 can increase the stability of the drill guide 1120.

Figure 12:
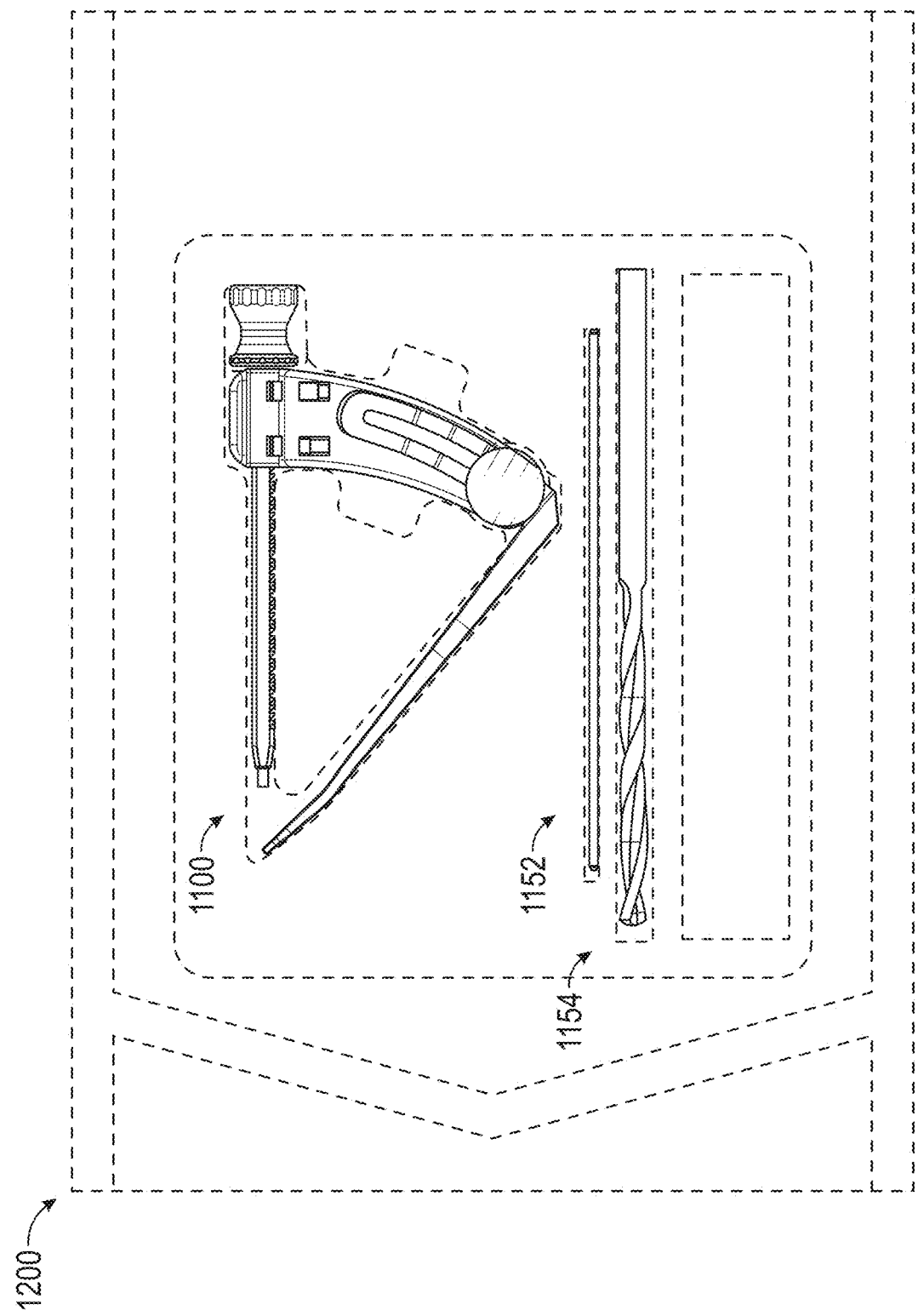
FIG. 12 shows an example of a kit for ACL repair.

FIG. 12 shows an example of a kit 1200 for ACL repair.

The kit 1200 can include an ACL repair guide 1100. The kit 1200 can include a pin 1152. In some examples, the pin 1152 can be a 2.4 mm pin. In some examples, the pin 1152 can be between 2 mm and 3 mm. In some examples, the pin 1152 can be between 1 mm and 5 mm. The kit 1200 can include a reamer 1154. In some examples, the reamer 1154 can be a low profile reamer. In some examples, the reamer 1154 can be 10 mm. In some examples, the reamer 1154 can be between 5 mm and 15 mm. In some examples, the reamer 1154 can be between 1 mm and 25 mm. In some examples, the ACL repair guide 1100 can be assembled in the kit 1200. In some examples, the ACL repair guide 1100 can be disassembled in the kit 1200.

ACL repair guide 1100 can have a lefthand reference member and/or a righthand reference member. In some examples, the kit 1200 can include a hook guide. In some examples, the kit 1200 can include a sterile pouch for containing one or more of the contents of the kit 1200. In some examples, the kit 1200 can include a sterile tray. In some examples, the kit 1200 can include a screwdriver.

Other Variations

While certain examples have been described, these examples have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some examples, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

Conditional language used herein, such as, among others, "can," "could", "might," "may," "e.g.," and the like, unless specifically stated otherwise, or otherwise understood within the context as used, is generally intended to convey that certain examples include, while certain examples do not include, certain features, elements and/or states. Thus, such conditional language is not generally intended to imply that features, elements and/or states are in any way required for one or more examples or that one or more examples necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain examples require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

Although the present disclosure includes certain examples, examples and applications, it will be understood by those skilled in the art that the present disclosure extends beyond the specifically disclosed examples to other alternative examples and/or uses and obvious modifications and equivalents thereof, including examples which do not provide all of the features and advantages set forth herein. Accordingly, the scope of the present disclosure is not intended to be limited by the specific disclosures of preferred examples herein, and may be defined by claims as presented herein or as presented in the future.

Headings are included herein for reference and to aid in locating various sections. These headings are not intended to limit the scope of the concepts described with respect thereto. Such concepts may have applicability throughout the entire specification.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A method of forming a tunnel in bone, comprising:
   providing an orthopedic tool, wherein the orthopedic tool comprises:
   a main body;
   a drill guide having a proximal end, a distal end, and a lumen extending from the proximal end to the distal end, the drill guide configured to engage the main body;
   a reference member having a distal end, the reference member configured to engage the main body, and the reference member comprising an engagement component on the distal end, the engagement component configured to engage a patient's bone; and
   adjusting an angle of the reference member relative to the drill guide;

introducing the reference member to a surgical site such that the reference member engages the patient's bone;
introducing the drill guide to a surgical site such that the drill guide engages the patient's bone;
engaging the drill guide with a plurality of locking components configured to selectively lock the drill guide in place with respect to the main body, the plurality of locking components comprising a plurality of spring-loaded caps configured to engage a threaded portion of the drill guide and a ball plunger configured to engage the drill guide; and
advancing a drill pin through the lumen of the drill guide such that a tunnel is formed in the patient's bone.

2. The method of claim 1, wherein adjusting the reference member relative to the drill guide comprises using a reference member knob to adjust a position of the reference member relative to the main body.

3. The method of claim 1, further comprising advancing a suture through the drill guide and the tunnel.

4. The method of claim 1, further comprising forcing a drill bit on the distal end of the drill guide into the patient's bone, the drill bit having a circular cross-section.

5. The method of claim 1, wherein positioning the plurality of locking components such that the drill guide is locked in place with respect to the main body comprises rotating the drill guide such that a plurality of grooves of the drill guide engages at least one locking component of the plurality of locking components.

6. An orthopedic tool, comprising:
a main body;
a drill guide having a proximal end, a distal end, and a lumen extending from the proximal end to the distal end, the drill guide configured to engage the main body;
a plurality of locking components configured to selectively lock the drill guide in place with respect to the main body, the plurality of locking components comprising a plurality of spring-loaded caps configured to engage a threaded portion of the drill guide and a ball plunger configured to engage the drill guide; and
a reference member having a distal end, the reference member configured to engage the main body, and the reference member comprising an engagement component on the distal end, the engagement component configured to engage a patient's bone,
wherein the reference member is moveable with respect to the main body.

7. The orthopedic tool of claim 6, further comprising a reference member knob configured to engage the main body and the reference member, the reference member knob configured to adjust a position of the reference member relative to the main body.

8. The orthopedic tool of claim 7, wherein the reference member knob is configured to adjust an angle of the reference member relative to the drill guide.

9. The orthopedic tool of claim 6, wherein the engagement component comprises curved components extending laterally from the distal end of the reference member.

10. The orthopedic tool of claim 6, further comprising a drill bit having a circular cross-section on a distal end of the drill guide.

11. The orthopedic tool of claim 6, wherein the reference member comprises a first arm configured to engage the main body, a second arm configured to engage the patient's bone, and an angle between the first arm and the second arm.

12. The orthopedic tool of claim 6, wherein the engagement component comprises a fork component.

13. A method of forming a tunnel in bone, comprising:
providing an orthopedic tool, wherein the orthopedic tool comprises:
a main body;
a drill guide having a proximal end, a distal end, and a lumen extending from the proximal end to the distal end, the drill guide configured to engage the main body;
a reference member having a distal end, the reference member configured to engage the main body, and the reference member comprising an engagement component on the distal end, the engagement component configured to engage a patient's bone; and
adjusting an angle of the reference member relative to the drill guide;
introducing the reference member to a surgical site such that the reference member engages the patient's bone;
introducing the drill guide to a surgical site such that the drill guide engages the patient's bone;
engaging the drill guide with a plurality of locking components configured to selectively lock the drill guide in place with respect to the main body, the plurality of locking components comprising a plurality of spring-loaded caps configured to engage a threaded portion of the drill guide and a ball plunger configured to engage the drill guide; and
advancing a drill pin through the lumen of the drill guide such that a tunnel is formed in the patient's bone.

14. The method of claim 13, wherein adjusting the reference member relative to the drill guide comprises using a reference member knob to adjust a position of the reference member relative to the main body.

15. The method of claim 13, further comprising advancing a suture through the drill guide and the tunnel.

16. The method of claim 13, further comprising forcing a drill bit on the distal end of the drill guide into the patient's bone, the drill bit having a circular cross-section.

17. The method of claim 13, wherein positioning the plurality of locking components such that the drill guide is locked in place with respect to the main body comprises rotating the drill guide such that a plurality of grooves of the drill guide engages at least one locking component of the plurality of locking components.

18. An orthopedic tool, comprising:
a main body;
a drill guide having a proximal end, a distal end, and a lumen extending from the proximal end to the distal end, the drill guide configured to engage the main body;
a plurality of locking components configured to selectively lock the drill guide in place with respect to the main body, the plurality of locking components comprising a plurality of spring-loaded caps configured to engage a threaded portion of the drill guide and a ball plunger configured to engage the drill guide; and a ball
a reference member having a distal end, the reference member configured to engage the main body, and the reference member comprising an engagement component on the distal end, the engagement component configured to engage a patient's bone, wherein the reference member is moveable with respect to the main body.

19. The orthopedic tool of claim 18, further comprising a reference member knob configured to engage the main body and the reference member, the reference member knob configured to adjust a position of the reference member relative to the main body.

20. The orthopedic tool of claim 19, wherein the reference member knob is configured to adjust an angle of the reference member relative to the drill guide.

21. The orthopedic tool of claim 18, wherein the engagement component comprises curved components extending laterally from the distal end of the reference member.

22. The orthopedic tool of claim 18, further comprising a drill bit having a circular cross-section on a distal end of the drill guide.

23. The orthopedic tool of claim 18, wherein the reference member comprises a first arm configured to engage the main body, a second arm configured to engage the patient's bone, and an angle between the first arm and the second arm.

24. The orthopedic tool of claim 18, wherein the engagement component comprises a fork component.

* * * * *